United States Patent [19]

Reyes et al.

[11] Patent Number: 5,436,318
[45] Date of Patent: Jul. 25, 1995

[54] HEPATITIS C VIRUS EPITOPES

[75] Inventors: Gregory Reyes; Jungsuh P. Kim, both of Palo Alto; Randolph Moeckli, Redwood City, all of Calif.

[73] Assignee: Genelabs Technologies, Inc., Redwood City, Calif.

[21] Appl. No.: 853,985

[22] Filed: Mar. 20, 1992

Related U.S. Application Data

[60] Division of Ser. No. 594,854, Oct. 9, 1990, abandoned, which is a continuation-in-part of Ser. No. 505,611, Apr. 6, 1990, abandoned.

[51] Int. Cl.$^6$ .................. C07K 15/04; C12Q 1/70; C12P 21/06; C07H 17/00
[52] U.S. Cl. .................................... 530/350; 530/826; 435/5; 435/697; 435/235.1; 435/320.1; 536/23.72
[58] Field of Search .................. 435/5, 6, 235.1, 320.1, 435/69.7; 536/27, 23.72; 530/350, 826

[56] References Cited

U.S. PATENT DOCUMENTS 4,464,474 8/1984 Coursaget .......................... 436/513

FOREIGN PATENT DOCUMENTS

| | | |
|---|---|---|
| 0293274 | 11/1988 | European Pat. Off. ...... C12N 15/00 |
| 0388232A1 | 3/1990 | European Pat. Off. . |
| 0414475A1 | 8/1990 | European Pat. Off. . |
| 0445423A2 | 12/1990 | European Pat. Off. . |
| 0442394A2 | 2/1991 | European Pat. Off. . |
| 2239245A | 6/1991 | United Kingdom . |
| WO82/00205 | 1/1982 | WIPO . |
| WO87/0593 | 10/1987 | WIPO . |
| WO90/00597 | 1/1990 | WIPO . |
| WO90/10060 | 9/1990 | WIPO . |
| WO91/15771 | 10/1991 | WIPO . |

OTHER PUBLICATIONS

Choo et al., "Genetic organization and diversity of the hepatitis C virus", Proc. Natl. Acad. Sci. 88:2451–55 (1991).
Choo et al., "Hepatitis C virus: The major causative agent of viral non-A, non-B hepatitis," Br. Med. Bull 46:423–441 (1990).
Miller et al., "Hepatitis C virus shares amino acid sequence simularity with postivirus and flairviruses as well as members of two plant virus supergroups," Proc. Natl. Acad. Sci 87:2057–2061 (1990).
Jacob, J. R., et al., J. Infect. Dis. 161:1121–1127 (1990).
Kuo, G., et al., Science 244:362 (1989).
Van Der Poel, C. L., et al., Lancet 337:317 (1991).

*Primary Examiner*—Michael P. Woodward
*Attorney, Agent, or Firm*—Gary R. Fabian; Peter J. Dehlinger

[57] ABSTRACT

Peptide antigens which are immunoreactive with sera from individuals infected with hepatitis C virus (HCV) are disclosed. Several of the antigens are immunologically reactive with antibodies present in individuals identified as having chronic and acute HCV infection. The antigens are useful in diagnostic methods for detecting HCV infection in humans. Also disclosed are corresponding genomic-fragment clones containing polynucleotides encoding the open reading frame sequences for the antigenic peptides.

1 Claim, 16 Drawing Sheets

```
GAA TTC CTC GTG CAA GCG TGG AAG TCC AAG AAA ACC CCA ATG GGG TTC
TCG TAT GAT ACC CGC TGC TTT GAC TCC ACA GTC ACT GAG AGC GAC ATC
CGT ACG GAG GAG GCA ATC TAC CAA TGT TGT GAC CTC GAC CCC CAA GCC
CGC GTG GCC ATC AAG TCC CTC ACC GAG AGG CTT TAT GTT GGG GGC CCT
CTT ACC AAT TCA AGG GGG GAG AAC TGC GGC TAT CGC AGG TGC CGC GCG
AGC GGC GTA CTG ACA ACT AGC TGT GGT AAC ACC CTC ACT TGC TAC ATC
AAG GCC CGG GCA GCC TGT CGA GCC GCA GGG CTC CAG GAC TGC ACC ATG
CTC GTG TGT GGC GAC GAC TTA GTC GTT ATC TGT GAA AGC GCG GGG GTC
CAG GAG GAC GCG GCG AGC CTG AGA GCC TTC ACG GAG GCT ATG ACC AGG
TAC TCC GCC CCC CCC GGG GAC CCC CCA CAA CCA GAA TAC GAC TTG GAG
CTC ATA ACA TCA TGC TCC TCC AAC GTG TCA GTC GCC CAC GAC GGC GCT
GGA AAG AGG GTC TAC TAC CTC ACC CGG
                                    ← R9
```

Fig. 3

```
GAA TTC TTC ACA GAA TTG GAC GGG GTG CGC CTA CAT AGG TTT GCG CCC
                                                    F7
CCC TGC AAG CCC TTG CTG CGG GAG GAG GTA TCA TTC AGA GTA GGA CTC
CAC GAA TAC CCG GTA GGG TCG CAA TTA CCT TGC GAG CCC GAA CCG GAT
GTG GCC GTG TTG ACG TCC ATG CTC ACT GAT CCC TCC CAT ATA ACA GCA
GAG GCG GCC GGG CGA AGG TTG GCG AGG GGA TCA CCC CCC TCT GTG GCC
AGC TCC TCG GCT AGC CAG CTA TCC GCT CCA TCT CTC AAG GCA ACT GCC
ACC GCT AAC CAT GAC TCC CCT GAT GCT GAG CTC ATA GAG GCC AAC CTC
CTA TGG AGG CAG GAG ATG GGC GGC AAC ATC ACC AGG GTT GAG TCA GAA
AAC AAA GTG GTG ATT CTG GAC TCC TTC GAT CCG CTT GTG GCG GAG GAG
GAC GAG CGG GAG ATC TCC GTA CCC GCA GAA ATC CTG CGG AAG TCT CGG
AGA TTC GCC CAG GCC CTG CCC GTT TGG GCG CGG CCG GAC TAT AAC CCC
CCG CTA GTG GAG ACG TGG AAA AAG CCC GAC TAC GAA CCA CCT GTG GTC
CAT GGC TGT CCG CTT CCA CCT CCA AAG TCC CCT CCT GTG CCT CCG CCT
CGG AAG AAG CGG ACG GTG GTC CTC ACT GAA TCA ACC CTA TCT ACT GCC
TTG GCC GAG CTC GCC ACC AGA AGC TTT GGC AGC TCC TCA ACT TCC GGC
ATT ACG GGC GAC AAT ACG ACA ACA TCC TCT GAG CCC GCC CCT TCT GGC
TGC CCC CCC GAC TCC GAC GCT GAG TCC TAT TCC TCC ATG CCC CCC CTG
GAG GGG GAG CCT GGG GAT CCG GAT CTT AGC GAC GGG TCA TGG TCA ACG
GTC AGT AGT GAG GCC AAC GCG GAG GAT GTC GTG TGC TGC TCA ATG TCT
         F8
TAC TCT TGG ACA GGC GCA CTC GTC ACC CCG TGC GCC GCG AAA GAA CAG
AAA CTG CCC ATC AAT GCA CTA AGC AAC TCG TTG CTA CGT CAC CAC AAT
TTG GTG TAT TCC ACC ACC TCA CGC AGT GCT TGC CAA AGG CAG AAG AAA
                                       R8
GTC ACA TTT GAC AGA CTG CAA GTT CTG GAC AGC ATT ACA GAC GTA
CTC AAG GAG GTT AAA GCA GCG GCG TCA AAA GTG AAG GCT AAC TTG CTA
TCC GTA GAG GAA GCT TGC AGC CTG ACG CCC CAC TCA GCC AAA TCC
AAG TTT GGT TAT GGG GCA AAA GAC GTC CGT TGC CAT GCC AGA AAG GCC
GTA ACC CAC ATC AAC TCC GTG TGG AAA GAC CTT CTG GAA GAC AAT GTA
ACA CCA ATA GAC ACT ACC ATC ATG GCT AAG AAC GAG GTT TTC TGC GTT
CAG CCT GAG AAG GGG GGT CGT AAG CCA GCT CGT CTC ATC GTG TTC CCC
GAT CTG GGC GTG CGC GTG TGC GAA AAG ATG GCT TTG TAC GAC GTG GTT
ACC AAG CTC CCC TTG GCC GTG ATG GGA AGC TCC TAC GGA TTC AAA TAC
TCA CCA GGA CAG CGG GTT GAA TTC
```

Fig. 4

■S  T   T   G   E   I   P   F   Y   G   K   A   I   P   L   E
CC ACC ACC GGA GAG ATC CCT TTT TAC GGC AAG GCT ATC CCC CTC GAA

V   I   K   G   G   R   H   L   I   F   C   H   S   K   K   K
GTA ATC AAG GGG GGG AGA CAT CTC ATC TTC TGT CAT TCA AAG AAG AAG

C   D   E   L   A   A   K   L   V   A   L   G   I   N   A   V
TGC GAC GAA CTC GCC GCA AAG CTG GTC GCA TTG GGC ATC AAT GCC GTG

A   Y   Y   R   G   L   D   V   S   V   I   P   T   S   G   D
GCC TAC TAC CGC GGT CTT GAC GTG TCC GTC ATC CCG ACC AGC GGC GAT

V   V   V   V   A   T   D   A   L   M   T   G   Y   T   G   D
GTT GTC GTC GTG GCA ACC GAT GCC CTC ATG ACC GGC TAT ACC GGC GAC

F   D   S   V   I   D   C   N   T   C   V   T   Q   T   V   D
TTC GAC TCG GTG ATA GAC TGC AAT ACG TGT GTC ACC CAG ACA GTC GAT

F   S   L   D   P   T   F   T   I   E   T   I   T   L   P   Q
TTC AGC CTT GAC CCT ACC TTC ACC ATT GAG ACA ATC ACG CTC CCC CAG

D   A   V   S   R   T   Q   R   R   G   R   T   G ■ R   G   K
GAT GCT GTC TCC CGC ACT CAA CGT CGG GGC AGG ACT GGC AGG GGG AAG

P   G   I   Y   R   F   V   A   P   G   E   R   P   S   G   M
CCA GGC ATC TAC AGA TTT GTG GCA CCG GGG GAG CGC CCC TCC GGC ATG

F   D   S   S   V   L   C   E   C   Y   D   A   G   C   A   W
TTC GAC TCG TCC GTC CTC TGT GAG TGC TAT GAC GCA GGC TGT GCT TGG

Y   E   L ▲ T   P   A   E   T   T   V   R   L   R   A   Y   M
TAT GAG CTC ACG CCC GCC GAG ACT ACA GTT AGG CTA CGA GCG TAC ATG

N   T   P   G   L   P   V   C   Q   D ✱
AAC ACC CCG GGG CTT CCC GTG TGC CAG GAC

```
GAA TTC CGC ACG CCC GCC GAG ACT ACA GTT AGG CTA CGG GCG TAC
45
Glu Phe Arg Thr Pro Ala Glu Thr Thr Val Arg Leu Arg Ala Tyr
15

ATG AAC ACT CCG GGG CTT CCC GTG TGC CAG GAC GGA ATT CCG TCC
90
Met Asn Thr Pro Gly Leu Pro Val Cys Gln Asp Gly Ilu Pro Ser
30

CCG TCC ACC ACC GGA GAG ATC CCT TTT TAC GGC AAG GCT ATC CCC
135
Pro Ser Thr Thr Gly Glu Ilu Pro Phe Tyr Gly Lys Ala Ilu Pro
45

CTC GAA GTA ATC AAG GGG GGA AGA CAT CTC ATC TTC TGT CAT TCA
180
Leu Glu Val Ilu Lys Gly Gly Arg His Leu Ilu Phe Cys His Ser
60

AAG AAG TGC GAC GAA CTC GCC GCA AAG CTG GTC GCA TTG GGC
225
Lys Lys Cys Asp Glu Leu Ala Ala Lys Leu Val Ala Leu Gly
75

ATC AAT GCC GTG GCC TAC TAC CGC GGT CTT GAC GTG TCC GTC ATC
270
Ilu Asn Ala Val Ala Tyr Tyr Arg Gly Leu Asp Val Ser Val Ilu
90
```

```
CCG ACC AGC GGC GAT GTT GTC GTG GCA ACC GAT GCC CTC ATG
315
Pro Thr Ser Gly Asp Val Val Val Ala Thr Asp Ala Leu Met
105

ACC GGC TAT ACC GGC GAC TTC GAC TCG GTG ATA GAC TGC AAT ACG
360
Thr Gly Tyr Thr Gly Asp Phe Asp Ser Val Ilu Asp Cys Asn Thr
120

TGT GTC ACC CAG ACA GTC GAT TTC AGC CTT GAC CCT ACC TTC ACC
405
Cys Val Thr Gln Thr Val Asp Phe Ser Leu Asp Pro Thr Phe Thr
135

ATT GAG ACA ATC ACG CTC CCC CAG GAT GCT GTC TCC CGC ACT CAA
450
Ilu Glu Thr Ilu Thr Leu Pro Gln Asp Ala Val Ser Arg Thr Gln
150

CGT CGG GGC AGG ACT GGC ACG GAA TTC 477
Arg Arg Gly Arg Thr Gly Thr Glu Phe 159
```

```
             10        20        30        40        50        60
              |         |         |         |         |         |
  1 CAGGCTGTCCTGAGAGGCTAGCCAGCTGCCGACCCCTTACCGATTTTGACCAGGGCTGGG
    GTCCGACAGGACTCTCCGATCGGTCGACGGCTGGGGAATGGCTAAAACTGGTCCCGACCC

61 GCCCTATCAGTTATGCCAACGGAAGCGGCCCCGACCAGCGCCCCTACTGCTGGCACTACC
    CGGGATAGTCAATACGGTTGCCTTCGCCGGGGCTGGTCGCGGGATGACGACCGTGATGG

121 CCCCAAAACCTTGCGGTATTGTGCCCGCGAAGAGTGTGTGTGGTCCGGTATATTGCTTCA
    GGGGTTTTGGAACGCCATAACACGGGCGCTTCTCACACACACCAGGCCATATAACGAAGT

181 CTCCCAGCCCCGTGGTGGTGGGAACGACCGACAGGTCGGGCGCGCCCACCTACAGCTGGG
    GAGGGTCGGGGCACCACCACCCTTGCTGGCTGTCCAGCCCGCGCGGGTGGATGTCGACCC

241 GTGAAAATGATACGGACGTCTTCGTCCTTAACAATACCAGGCCACCGCTGGGCAATTGGT
    CACTTTTACTATGCCTGCAGAAGCAGGAATTGTTATGGTCCGGTGGCGACCCGTTAACCA

301 TCGGTTGTACCTGGATGAACTCAACTGGATTCACCAAAGTGTGCGGAGCGCCTCCTTGTG
    AGCCAACATGGACCTACTTGAGTTGACCTAAGTGGTTTCACACGCCTCGCGGAGGAACAC

361 TCATCGGAGGGGCGGGCAACAACACCCTGCACTGCCCCACTGATTGCTTCCGCAAGCATC
    AGTAGCCTCCCCGCCCGTTGTTGTGGGACGTGACGGGGTGACTAACGAAGGCGTTCGTAG

421 CGGACGCCACATACTCTCGGTGCGGCTCCGGTCCCTGGATCACACCCAGGTGCCTGGTCG
    GCCTGCGGTGTATGAGAGCCACGCCGAGGCCAGGGACCTAGTGTGGGTCCACGGACCAGC

481 ACTACCCGTATAGGCTTTGGCTTTGGCATTGTACCATCAACTACACCATATTTAAAATCA
    TGATGGGCATATCCGAAACCGAAACCGTAACATGGTAGTTGATGTGGTATAAATTTTAGT

541 GGATGTACGTGGGAGGGGTCGAACACAGGCTGGAAGCTGCCTGCAACTGGACGCGGGGCG
    CCTACATGCACCCTCCCCAGCTTGTGTCCGACCTTCGACGGACGTTGACCTGCGCCCCGC

601 AACGTTGCGATCTGGAAGACAGGGACAGGTCCGAGCTCAGCCCGTTACTGCTGACCACTA
    TTGCAACGCTAGACCTTCTGTCCCTGTCCAGGCTCGAGTCGGGCAATGACGACTGGTGAT

661 CACAGTGGCAGGTCCTCCCGTGTTCCTTCACAACCCTACCAGCCTTGTCCACCGGCCTCA
    GTGTCACCGTCCAGGAGGGCACAAGGAAGTGTTGGGATGGTCGGAACAGGTGGCCGGAGT

721 TCCACCTCCACCAGAACATTGTGGACGTGCAGTACTTGTACGGGGTGGGGTCAAGCATCG
    AGGTGGAGGTGGTCTTGTAACACCTGCACGTCATGAACATGCCCCACCCCAGTTCGTAGC

781 CGTCCTGGGCCATTAAGTGGGAGTACGTCGTTCTCCTGTTCCTTCTGCTTGCAGACGCGC
    GCAGGACCCGGTAATTCACCCTCATGCAGCAAGAGGACAAGGAAGACGAACGTCTGCGCG

841 GCGTCTGCTCCTGCTTGTGGATGATGCTACTCATATCCCAAGCGGAGGCGGCTTTGGAGA
    CGCAGACGAGGACGAACACCTACTACGATGAGTATAGGGTTCGCCTCCGCCGAAACCTCT

901 ACCTCGTAATACTTAATGCAGCATCCCTGGCCGGGACGCACGGTCTTGTATCCTTCCTCG
    TGGAGCATTATGAATTACGTCGTAGGGACCGGCCCTGCGTGCCAGAACATAGGAAGGAGC
```

Fig. 8B

```
 961 TGTTCTTCTGCTTTGCATGGTATTTGAAGGGTAAGTGGGTGCCCGGAGCGGTCTACACCT
     ACAAGAAGACGAAACGTACCATAAACTTCCCATTCACCCACGGGCCTCGCCAGATGTGGA

1021 TCTACGGGATGTGGCCTCTCCTCCTGCTCCTGTTGGCGTTGCCCCAGCGGGCGTACGCGC
     AGATGCCCTACACCGGAGAGGAGGACGAGGACAACCGCAACGGGGTCGCCCGCATGCGCG

1081 TGGACACGGAGGTGGCCGCGTCGTGTGGCGGTGTTGTTCTCGTCGGGTTGATGGCGCTGA
     ACCTGTGCCTCCACCGGCGCAGCACACCGCCACAACAAGAGCAGCCCAACTACCGCGACT

1141 CTCTGTCACCATATTACAAGCGCTATATCAGCTGGTGCTTGTGGTGGCTTCAGTATTTTC
     GAGACAGTGGTATAATGTTCGCGATATAGTCGACCACGAACACCACCGAAGTCATAAAAG

1201 TGACCAGAGTGGAAGCGCAACTGCACGTGTGGATTCCCCCCCTCAACGTCCGAGGGGGGC
     ACTGGTCTCACCTTCGCGTTGACGTGCACACCTAAGGGGGGAGTTGCAGGCTCCCCCCG

1261 GCGACGCCGTCATCTTACTCATGTGTGCTGTACACCCGACTCTGGTATTTGACATCACCA
     CGCTGCGGCAGTAGAATGAGTACACACGACATGTGGGCTGAGACCATAAACTGTAGTGGT

1321 AATTGCTGCTGGCCGTCTTCGGACCCCTTTGGATTCTTCAAGCCAGTTTGCTTAAAGTAC
     TTAACGACGACCGGCAGAAGCCTGGGGAAACCTAAGAAGTTCGGTCAAACGAATTTCATG

1381 CCTACTTTGTGCGCGTCCAAGGCCTTCTCCGGTTCTGCGCGTTAGCGCGGAAGATGATCG
     GGATGAAACACGCGCAGGTTCCGGAAGAGGCCAAGACGCGCAATCGCGCCTTCTACTAGC

1441 GAGGCCATTACGTGCAAATGGTCATCATTAAGTTAGGGGCGCTTACTGGCACCTATGTTT
     CTCCGGTAATGCACGTTTACCAGTAGTAATTCAATCCCCGCGAATGACCGTGGATACAAA

1501 ATAACCATCTCACTCCTCTTCGGGACTGGGCGCACAACGGCTTGCGAGATCTGGCCGTGG
     TATTGGTAGAGTGAGGAGAAGCCCTGACCCGCGTGTTGCCGAACGCTCTAGACCGGCACC

1561 CTGTAGAGCCAGTCGTCTTCTCCCAAATGGAGACCAAGCTCATCACGTGGGGGGCAGATA
     GACATCTCGGTCAGCAGAAGAGGGTTTACCTCTGGTTCGAGTAGTGCACCCCCGTCTAT

1621 CCGCCGCGTGCGGTGACATCATCAACGGCTTGCCTGTTTCCGCCCGCAGGGGCCGGGAGA
     GGCGGCGCACGCCACTGTAGTAGTTGCCGAACGGACAAAGGCGGGCGTCCCCGGCCCTCT

1681 TACTGCTCGGGCCAGCCGATGGAATGGTCTCCAAGGGGTGGAGGTTGCTGGCGCCCATCA
     ATGACGAGCCCGGTCGGCTACCTTACCAGAGGTTCCCCACCTCCAACGACCGCGGGTAGT

1741 CGGCGTACGCCCAGCAGACAAGGGGCCTCCTAGGGTGCATAATCACCAGCCTAACTGGCC
     GCCGCATGCGGGTCGTCTGTTCCCCGGAGGATCCCACGTATTAGTGGTCGGATTGACCGG

1801 GGGACAAAAACCAAGTGGAGGGTGAGGTCCAGATTGTGTCAACTGCTGCCCAAACCTTCC
     CCCTGTTTTTGGTTCACCTCCCACTCCAGGTCTAACACAGTTGACGACGGGTTTGGAAGG

1861 TGGCAACGTGCATCAATGGGGTGTGCTGGACTGTCTACCACGGGGCCGGAACGAGGACCA
     ACCGTTGCACGTAGTTACCCCACACGACCTGACAGATGGTGCCCCGGCCTTGCTCCTGGT
```

Fig. 8C

```
1921 TCGCGTCACCCAAGGGTCCTGTCATCCAGATGTATACCAATGTAGACCAAGACCTTGTGG
     AGCGCAGTGGGTTCCCAGGACAGTAGGTCTACATATGGTTACATCTGGTTCTGGAACACC

1981 GCTGGCCCGCTCCGCAAGGTAGCCGCTCATTGACACCCTGCACTTGCGGCTCCTCGGACC
     CGACCGGGCGAGGCGTTCCATCGGCGAGTAACTGTGGGACGTGAACGCCGAGGAGCCTGG

2041 TTTACCTGGTCACGAGGCACGCCGATGTCATTCCCGTGCGCCGGCGGGTGATAGCAGGG
     AAATGGACCAGTGCTCCGTGCGGCTACAGTAAGGGCACGCGGCCGCCCCACTATCGTCCC

2101 GCAGCCTGCTGTCGCCCCGGCCCATTTCCTACTTGAAAGGCTCCTCGGGGGTCCGCTGT
     CGTCGGACGACAGCGGGGCCGGGTAAAGGATGAACTTTCCGAGGAGCCCCCCAGGCGACA

2161 TGTGCCCCGCGGGGCACGCCGTGGGCATATTTAGGGCCGCGGTGTGCACCCGTGGAGTGG
     ACACGGGGCGCCCCGTGCGGCACCCGTATAAATCCCGGCGCCACACGTGGGCACCTCACC

2221 CTAAGGCGGTGGACTTTATCCCTGTGGAGAACCTAGAGACAACCATGAGGTCCCCGGTGT
     GATTCCGCCACCTGAAATAGGGACACCTCTTGGATCTCTGTTGGTACTCCAGGGGCCACA

2281 TCACGGATAACTCCTCTCCACCAGTAGTGCCCCAGAGCTTCCAGGTGGCTCACCTCCATG
     AGTGCCTATTGAGGAGAGGTGGTCATCACGGGGTCTCGAAGGTCCACCGAGTGGAGGTAC

2341 CTCCCACAGGCAGCGGCAAAAGCACCAAGGTCCCGGCTGCATATGCAGCTCAGGGCTATA
     GAGGGTGTCCGTCGCCGTTTTCGTGGTTCCAGGGCCGACGTATACGTCGAGTCCCGATAT

2401 AGGTGCTAGTACTCAACCCCTCTGTTGCTGCAACACTGGGCTTTGGTGCTTACATGTCCA
     TCCACGATCATGAGTTGGGGAGACAACGACGTTGTGACCCGAAACCACGAATGTACAGGT

2461 AGGCTCATGGGATCGATCCTAACATCAGGACCGGGGTGAGAACAATTACCACTGGCAGCC
     TCCGAGTACCCTAGCTAGGATTGTAGTCCTGGCCCCACTCTTGTTAATGGTGACCGTCGG

2521 CCATCACGTACTCCACCTACGGCAAGTTCCTTGCCGACGGCGGGTGCTCGGGGGGCGCTT
     GGTAGTGCATGAGGTGGATGCCGTTCAAGGAACGGCTGCCGCCCACGAGCCCCCGCGAA

2581 ATGACATAATAATTTGTGACGAGTGCCACTCCACGGATGCCACATCCATCTTGGGCATCG
     TACTGTATTATTAAACACTGCTCACGGTGAGGTGCCTACGGTGTAGGTAGAACCCGTAGC

2641 GCACTGTCCTTGACCAAGCAGAGACTGCGGGGGCGAGACTGGTTGTGCTCGCCACCGCCA
     CGTGACAGGAACTGGTTCGTCTCTGACGCCCCGCTCTGACCAACACGAGCGGTGGCGGT

2701 CCCCTCCGGGCTCCGTCACTGTGCCCCATCCCAACATCGAGGAGGTTGCTCTGTCCACCA
     GGGGAGGCCCGAGGCAGTGACACGGGGTAGGGTTGTAGCTCCTCCAACGAGACAGGTGGT

2761 CCGGAGAGATCCCTTTTTACGGCAAGGCTATCCCCCTCGAAGTAATCAAGGGGGGAGAC
     GGCCTCTCTAGGGAAAAATGCCGTTCCGATAGGGGGAGCTTCATTAGTTCCCCCCCTCTG

2821 ATCTCATCTTCTGTCATTCAAAGAAGAAGTGCGACGAACTCGCCGCAAAGCTGGTCGCAT
     TAGAGTAGAAGACAGTAAGTTTCTTCTTCACGCTGCTTGAGCGGCGTTTCGACCAGCGTA

2881 TGGGCATCAATGCCGTGGCCTACTACCGCGGTCTTGACGTGTCCGTCATCCCGACCAGCG
     ACCCGTAGTTACGGCACCGGATGATGGCGCCAGAACTGCACAGGCAGTAGGGCTGGTCGC
```

Fig. 8D

```
2941 GCGATGTTGTCGTCGTGGCAACCGATGCCCTCATGACCGGCTATACCGGCGACTTCGACT
     CGCTACAACAGCAGCACCGTTGGCTACGGGAGTACTGGCCGATATGGCCGCTGAAGCTGA

3001 CGGTGATAGACTGCAATACGTGTGTCACCCAGACAGTCGATTTCAGCCTTGACCCTACCT
     GCCACTATCTGACGTTATGCACACAGTGGGTCTGTCAGCTAAAGTCGGAACTGGGATGGA

3061 TCACCATTGAGACAATCACGCTCCCCCAGGATGCTGTCTCCCGCACTCAACGTCGGGGCA
     AGTGGTAACTCTGTTAGTGCGAGGGGGTCCTACGACAGAGGGCGTGAGTTGCAGCCCCGT

3121 GGACTGGCAGGGGGAAGCCAGGCATCTACAGATTTGTGGCACCGGGGGAGCGCCCCTCCG
     CCTGACCGTCCCCCTTCGGTCCGTAGATGTCTAAACACCGTGGCCCCCTCGCGGGGAGGC

3181 GCATGTTCGACTCGTCCGTCCTCTGTGAGTGCTATGACGCAGGCTGTGCTTGGTATGAGC
     CGTACAAGCTGAGCAGGCAGGAGACACTCACGATACTGCGTCCGACACGAACCATACTCG

3241 TCACGCCCGCCGAGACTACAGTTAGGCTACGAGCGTACATGAACACCCCGGGGCTTCCCG
     AGTGCGGGCGGCTCTGATGTCAATCCGATGCTCGCATGTACTTGTGGGCCCCGAAGGGC

3301 TGTGCCAGGACCATCTTGAATTTTGGGAGGGCGTCTTTACAGGCCTCACTCATATAGATG
     ACACGGTCCTGGTAGAACTTAAAACCCTCCCGCAGAAATGTCCGGAGTGAGTATATCTAC

3361 CCCACTTTCTATCCCAGACAAAGCAGAGTGGGGAGAACCTTCCTTACCTGGTAGCGTACC
     GGGTGAAAGATAGGGTCTGTTTCGTCTCACCCCTCTTGGAAGGAATGGACCATCGCATGG

3421 AAGCCACCGTGTGCGCTAGGGCTCAAGCCCCTCCCCCATCGTGGGACCAGATGTGGAAGT
     TTCGGTGGCACACGCGATCCCGAGTTCGGGGAGGGGGTAGCACCCTGGTCTACACCTTCA

3481 GTTTGATTCGCCTCAAGCCCACCCTCCATGGGCCAACACCCCTGCTATACAGACTGGGCG
     CAAACTAAGCGGAGTTCGGGTGGGAGGTACCCGGTTGTGGGACGATATGTCTGACCCGC

3541 CTGTTCAGAATGAAATCACCCTGACGCACCCAGTCACCAAATACATCATGACATGCATGT
     GACAAGTCTTACTTTAGTGGGACTGCGTGGGTCAGTGGTTTATGTAGTACTGTACGTACA

3601 CGGCCGACCTGGAGGTCGTCACGAGCACCTGGGTGCTCGTTGGCGGCGTCCTGGCTGCTT
     GCCGGCTGGACCTCCAGCAGTGCTCGTGGACCCACGAGCAACCGCCGCAGGACCGACGAA

3661 TGGCCGCGTATTGCCTGTCAACAGGCTGCGTGGTCATAGTGGGCAGGGTCGTCTTGTCCG
     ACCGGCGCATAACGGACAGTTGTCCGACGCACCAGTATCACCCGTCCCAGCAGAACAGGC

3721 GGAAGCCGGCAATCATACCTGACAGGGAAGTCCTCTACCGAGAGTTCGATGAGATGGAAG
     CCTTCGGCCGTTAGTATGGACTGTCCCTTCAGGAGATGGCTCTCAAGCTACTCTACCTTC

3781 AGTGCTCTCAGCACTTACCGTACATCGAGCAAGGGATGATGCTCGCCGAGCAGTTCAAGC
     TCACGAGAGTCGTGAATGGCATGTAGCTCGTTCCCTACTACGAGCGGCTCGTCAAGTTCG

3841 AGAAGGCCCTCGGCCTCCTGCAGACCGCGTCCCGTCAGGCAGAGGTTATCGCCCCTGCTG
     TCTTCCGGGAGCCGGAGGACGTCTGGCGCAGGGCAGTCCGTCTCCAATAGCGGGGACGAC
```

Fig. 8E

```
3901 TCCAGACCAACTGGCAAAAACTCGAGACCTTCTGGGCGAAGCATATGTGGAACTTCATCA
     AGGTCTGGTTGACCGTTTTTGAGCTCTGGAAGACCCGCTTCGTATACACCTTGAAGTAGT

3961 GTGGGATACAATACTTGGCGGGCTTGTCAACGCTGCCTGGTAACCCCGCCATTGCTTCAT
     CACCCTATGTTATGAACCGCCCGAACAGTTGCGACGGACCATTGGGGCGGTAACGAAGTA

4021 TGATGGCTTTTACAGCTGCTGTCACCAGCCCACTAACCACTAGCCAAACCCTCCTCTTCA
     ACTACCGAAAATGTCGACGACAGTGGTCGGGTGATTGGTGATCGGTTTGGGAGGAGAAGT

4081 ACATATTGGGGGGGTGGGTGGCTGCCCAGCTCGCCGCCCCGGTGCCGCTACTGCCTTTG
     TGTATAACCCCCCCACCCACCGACGGGTCGAGCGGCGGGGGCCACGGCGATGACGGAAAC

4141 TGGGCGCTGGCTTAGCTGGCGCCGCCATCGGCAGTGTTGGACTGGGGAAGGTCCTCATAG
     ACCCGCGACCGAATCGACCGCGGCGGTAGCCGTCACAACCTGACCCCTTCCAGGAGTATC

4201 ACATCCTTGCAGGGTATGGCGCGGGCGTGGCGGGAGCTCTTGTGGCATTCAAGATCATGA
     TGTAGGAACGTCCCATACCGCGCCCGCACCGCCCTCGAGAACACCGTAAGTTCTAGTACT

4261 GCGGTGAGGTCCCCTCCACGGAGGACCTGGTCAATCTACTGCCCGCCATCCTCTCGCCCG
     CGCCACTCCAGGGGAGGTGCCTCCTGGACCAGTTAGATGACGGGCGGTAGGAGAGCGGGC

4321 GAGCCCTCGTAGTCGGCGTGGTCTGTGCAGCAATACTGCGCCGGCACGTTGGCCCGGGCG
     CTCGGGAGCATCAGCCGCACCAGACACGTCGTTATGACGCGGCCGTGCAACCGGGCCCGC

4381 AGGGGGCAGTGCAGTGGATGAACCGGCTGATAGCCTTCGCCTCCCGGGGGAACCATGTTT
     TCCCCCGTCACGTCACCTACTTGGCCGACTATCGGAAGCGGAGGGCCCCCTTGGTACAAA

4441 CCCCCACGCACTACGTGCCGGAGAGCGATGCAGCTGCCCGCGTCACTGCCATACTCAGCA
     GGGGGTGCGTGATGCACGGCCTCTCGCTACGTCGACGGGCGCAGTGACGGTATGAGTCGT

4501 GCCTCACTGTAACCCAGCTCCTGAGGCGACTGCACCAGTGGATAAGCTCGGAGTGTACCA
     CGGAGTGACATTGGGTCGAGGACTCCGCTGACGTGGTCACCTATTCGAGCCTCACATGGT

4561 CTCCATGCTCCGGTTCCTGGCTAAGGGACATCTGGGACTGGATATGCGAGGTGTTGAGCG
     GAGGTACGAGGCCAAGGACCGATTCCCTGTAGACCCTGACCTATACGCTCCACAACTCGC

4621 ACTTTAAGACCTGGCTAAAAGCTAAGCTCATGCCACAGCTGCCTGGGATCCCCTTTGTGT
     TGAAATTCTGGACCGATTTTCGATTCGAGTACGGTGTCGACGGACCCTAGGGGAAACACA

4681 CCTGCCAGCGCGGGTATAAGGGGGTCTGGCGAGTGGACGGCATCATGCACACTCGCTGCC
     GGACGGTCGCGCCCATATTCCCCCAGACCGCTCACCTGCCGTAGTACGTGTGAGCGACGG

4741 ACTGTGGAGCTGAGATCACTGGACATGTCAAAAACGGGACGATGAGGATCGTCGGTCCTA
     TGACACCTCGACTCTAGTGACCTGTACAGTTTTTGCCCTGCTACTCCTAGCAGCCAGGAT

4801 GGACCTGCAGGAACATGTGGAGTGGGACCTTCCCCATTAATGCCTACACCACGGGCCCCT
     CCTGGACGTCCTTGTACACCTCACCCTGGAAGGGGTAATTACGGATGTGGTGCCCGGGGA

4861 GTACCCCCCTTCCTGCGCCGAACTACACGTTCGCGCTATGGAGGGTGTCTGCAGAGGAAT
     CATGGGGGGAAGGACGCGGCTTGATGTGCAAGCGCGATACCTCCCACAGACGTCTCCTTA
```

Fig. 8F

```
4921 ATGTGGAGATAAGGCAGGTGGGGGACTTCCACTACGTGACGGGTATGACTACTGACAATC
     TACACCTCTATTCCGTCCACCCCCTGAAGGTGATGCACTGCCCATACTGATGACTGTTAG

4981 TCAAATGCCCGTGCCAGGTCCCATCGCCCGAATTTTTCACAGAATTGGACGGGGTGCGCC
     AGTTTACGGGCACGGTCCAGGGTAGCGGGCTTAAAAAGTGTCTTAACCTGCCCCACGCGG

5041 TACATAGGTTTGCGCCCCCCTGCAAGCCCTTGCTGCGGGAGGAGGTATCATTCAGAGTAG
     ATGTATCCAAACGCGGGGGGACGTTCGGGAACGACGCCCTCCTCCATAGTAAGTCTCATC

5101 GACTCCACGAATACCCGGTAGGGTCGCAATTACCTTGCGAGCCCGAACCGGACGTGGCCG
     CTGAGGTGCTTATGGGCCATCCCAGCGTTAATGGAACGCTCGGGCTTGGCCTGCACCGGC

5161 TGTTGACGTCCATGCTCACTGATCCCTCCCATATAACAGCAGAGGCGGCCGGGCGAAGGT
     ACAACTGCAGGTACGAGTGACTAGGGAGGGTATATTGTCGTCTCCGCCGGCCCGCTTCCA

5221 TGGCGAGGGGATCACCCCCCTCTGTGGCCAGCTCCTCGGCTAGCCAGCTATCCGCTCCAT
     ACCGCTCCCCTAGTGGGGGGAGACACCGGTCGAGGAGCCGATCGGTCGATAGGCGAGGTA

5281 CTCTCAAGGCAACTTGCACCGCTAACCATGACTCCCCTGATGCTGAGCTCATAGAGGCCA
     GAGAGTTCCGTTGAACGTGGCGATTGGTACTGAGGGGACTACGACTCGAGTATCTCCGGT

5341 ACCTCCTATGGAGGCAGGAGATGGGCGGCAACATCACCAGGGTTGAGTCAGAAAACAAAG
     TGGAGGATACCTCCGTCCTCTACCCGCCGTTGTAGTGGTCCCAACTCAGTCTTTTGTTTC

5401 TGGTGATTCTGGACTCCTTCGATCCGCTTGTGGCGGAGGAGGACGAGCGGGAGATCTCCG
     ACCACTAAGACCTGAGGAAGCTAGGCGAACACCGCCTCCTCCTGCTCGCCCTCTAGAGGC

5461 TACCCGCAGAAATCCTGCGGAAGTCTCGGAGATTCGCCCAGGCCCTGCCCGTTTGGGCGC
     ATGGGCGTCTTTAGGACGCCTTCAGAGCCTCTAAGCGGGTCCGGGACGGGCAAACCCGCG

5521 GGCCGGACTATAACCCCCCGCTAGTGGAGACGTGGAAAAAGCCCGACTACGAACCACCTG
     CCGGCCTGATATTGGGGGGCGATCACCTCTGCACCTTTTTCGGGCTGATGCTTGGTGGAC

5581 TGGTCCATGGCTGTCCGCTTCCACCTCCAAAGTCCCCTCCTGTGCCTCCGCCTCGGAAGA
     ACCAGGTACCGACAGGCGAAGGTGGAGGTTTCAGGGGAGGACACGGAGGCGGAGCCTTCT

5641 AGCGGACGGTGGTCCTCACTGAATCAACCCTATCTACTGCCTTGGCCGAGCTCGCCACCA
     TCGCCTGCCACCAGGAGTGACTTAGTTGGGATAGATGACGGAACCGGCTCGAGCGGTGGT

5701 GAAGCTTTGGCAGCTCCTCAACTTCCGGCATTACGGGCGACAATACGACAACATCCTCTG
     CTTCGAAACCGTCGAGGAGTTGAAGGCCGTAATGCCCGCTGTTATGCTGTTGTAGGAGAC

5761 AGCCCGCCCCTTCTGGCTGCCCCCCCGACTCCGACGCTGAGTCCTATTCCTCCATGCCCC
     TCGGGCGGGGAAGACCGACGGGGGGGCTGAGGCTGCGACTCAGGATAAGGAGGTACGGGG

5821 CCCTGGAGGGGGAGCCTGGGGATCCGGATCTTAGCGACGGGTCATGGTCAACGGTCAGTA
     GGGACCTCCCCCTCGGACCCCTAGGCCTAGAATCGCTGCCCAGTACCAGTTGCCAGTCAT
```

Fig. 8G

```
5881 GTGAGGCCAACGCGGAGGATGTCGTGTGCTGCTCAATGTCTTACTCTTGGACAGGCGCAC
     CACTCCGGTTGCGCCTCCTACAGCACACGACGAGTTACAGAATGAGAACCTGTCCGCGTG

5941 TCGTCACCCCGTGCGCCGCGGAAGAACAGAAACTGCCCATCAATGCACTAAGCAACTCGT
     AGCAGTGGGGCACGCGGCGCCTTCTTGTCTTTGACGGGTAGTTACGTGATTCGTTGAGCA

6001 TGCTACGTCACCACAATTTGGTGTATTCCACCACCTCACGCAGTGCTTGCCAAAGGCAGA
     ACGATGCAGTGGTGTTAAACCACATAAGGTGGTGGAGTGCGTCACGAACGGTTTCCGTCT

6061 AGAAAGTCACATTTGACAGACTGCAAGTTCTGGACAGCCATTACCAGGACGTACTCAAGG
     TCTTTCAGTGTAAACTGTCTGACGTTCAAGACCTGTCGGTAATGGTCCTGCATGAGTTCC

6121 AGGTTAAAGCAGCGGCGTCAAAAGTGAAGGCTAACTTGCTATCCGTAGAGGAAGCTTGCA
     TCCAATTTCGTCGCCGCAGTTTTCACTTCCGATTGAACGATAGGCATCTCCTTCGAACGT

6181 GCCTGACGCCCCACACTCAGCCAAATCCAAGTTTGGTTATGGGGCAAAAGACGTCCGTT
     CGGACTGCGGGGGTGTGAGTCGGTTTAGGTTCAAACCAATACCCCGTTTTCTGCAGGCAA

6241 GCCATGCCAGAAAGGCCGTAACCCACATCAACTCCGTGTGGAAAGACCTTCTGGAAGACA
     CGGTACGGTCTTTCCGGCATTGGGTGTAGTTGAGGCACACCTTTCTGGAAGACCTTCTGT

6301 ATGTAACACCAATAGACACTACCATCATGGCTAAGAACGAGGTTTTCTGCGTTCAGCCTG
     TACATTGTGGTTATCTGTGATGGTAGTACCGATTCTTGCTCCAAAAGACGCAAGTCGGAC

6361 AGAAGGGGGGTCGTAAGCCAGCTCGTCTCATCGTGTTCCCCGATCTGGGCGTGCGCGTGT
     TCTTCCCCCCAGCATTCGGTCGAGCAGAGTAGCACAAGGGGCTAGACCCGCACGCGCACA

6421 GCGAAAAGATGGCTTTGTACGACGTGGTTACAAAGCTCCCCTTGGCCGTGATGGGAAGCT
     CGCTTTTCTACCGAAACATGCTGCACCAATGTTTCGAGGGGAACCGGCACTACCCTTCGA

6481 CCTACGGATTCCAATACTCACCAGGACAGCGGGTTGAATTCCTCGTGCAAGCGTGGAAGT
     GGATGCCTAAGGTTATGAGTGGTCCTGTCGCCCAACTTAAGGAGCACGTTCGCACCTTCA

6541 CCAAGAAAACCCCAATGGGGTTCTCGTATGATACCCGCTGCTTTGACTCCACAGTCACTG
     GGTTCTTTTGGGGTTACCCCAAGAGCATACTATGGGCGACGAAACTGAGGTGTCAGTGAC

6601 AGAGCGACATCCGTACGGAGGAGGCAATCTACCAATGTTGTGACCTCGACCCCCAAGCCC
     TCTCGCTGTAGGCATGCCTCCTCCGTTAGATGGTTACAACACTGGAGCTGGGGGTTCGGG

6661 GCGTGGCCATCAAGTCCCTCACCGAGAGGCTTTATGTTGGGGCCCTCTTACCAATTCAA
     CGCACCGGTAGTTCAGGGAGTGGCTCTCCGAAATACAACCCCGGGAGAATGGTTAAGTT

6721 GGGGGGAGAACTGCGGCTATCGCAGGTGCCGCGCGAGCGGCGTACTGACAACTAGCTGTG
     CCCCCCTCTTGACGCCGATAGCGTCCACGGCGCGCTCGCCGCATGACTGTTGATCGACAC

6781 GTAACACCCTCACTTGCTACATCAAGGCCCGGGCAGCCTGTCGAGCCGCAGGGCTCCAGG
     CATTGTGGGAGTGAACGATGTAGTTCCGGGCCCGTCGGACAGCTCGGCGTCCCGAGGTCC

6841 ACTGCACCATGCTCGTGTGTGGCGACGACTTAGTCGTTATCTGTGAAAGCGCGGGGGTCC
     TGACGTGGTACGAGCACACACCGCTGCTGAATCAGCAATAGACACTTTCGCGCCCCCAGG
```

Fig. 8H

```
6901 AGGAGGACGCGGCGAGCCTGAGAGCCTTCACGGAGGCTATGACCAGGTACTCCGCCCCCC
     TCCTCCTGCGCCGCTCGGACTCTCGGAAGTGCCTCCGATACTGGTCCATGAGGCGGGGG

6961 CTGGGGACCCCCACAACCAGAATACGACTTGGAGCTCATAACATCATGCTCCTCCAACG
     GACCCCTGGGGGGTGTTGGTCTTATGCTGAACCTCGAGTATTGTAGTACGAGGAGGTTGC

7021 TGTCAGTCGCCCACGACGGCGCTGGAAAGAGGGTCTACTACCTCACCCGTGACCCTACAA
     ACAGTCAGCGGGTGCTGCCGCGACCTTTCTCCCAGATGATGGAGTGGGCACTGGGATGTT

7081 CCCCCCTCGCGAGAGCTGCGTGGGAGACAGCAAGACACACTCCAGTCAATTCCTGGCTAG
     GGGGGGAGCGCTCTCGACGCACCCTCTGTCGTTCTGTGTGAGGTCAGTTAAGGACCGATC

7141 GCAACATAATCATGTTTGCCCCCACACTGTGGGCGAGGATGATACTGATGACCCATTTCT
     CGTTGTATTAGTACAAACGGGGGTGTGACACCCGCTCCTACTATGACTACTGGGTAAAGA

7201 TTAGCGTCCTTATAGCCAGGGACCAGCTTGAACAGGCCCTCGATTGCGAGATCTACGGGG
     AATCGCAGGAATATCGGTCCCTGGTCGAACTTGTCCGGGAGCTAACGCTCTAGATGCCCC

7261 CCTGCTACTCCATAGAACCACTTGATCTACCTCCAATCATTCAAAGACTC
     GGACGATGAGGTATCTTGGTGAACTAGATGGAGGTTAGTAAGTTTCTGAG
```

HEPATITIS C VIRUS EPITOPES

This application is a divisional of application Ser. No. 07/594,854, abandoned, filed Oct. 9, 1990, which is a continuation-in-part of application Ser. No. 07/505,611, filed Apr. 6, 1990, abandoned.

FIELD OF INVENTION

This invention relates to specific peptide vital antigens which are immunoreactive with sera from patients infected with parenterally transmitted non-A, non-B hepatitis (PT-NANBH) virus, to polynucleotide sequences which encode the peptides, to an expression system capable of producing the peptides, and to methods of using the peptides for detecting PT-NANBH infection in human sera.

REFERENCES

Bradley, D. W., et al., J. Infec. Dis., 148:2 (1983).
Bradley, D. W., et al., J Gen. Virol., 69:1 (1988).
Bradley, D. W. et al., Proc. Nat. Acad. Sci., USA, 84:6277 (1987).
Chomczynski, P., et al., Anal Biochem, 162:156 (1987).
Choo, Q. -L., et al, Science, 244:359 (1989).
Current Protocols in Molecular Biology, Wiley Interscience, Chapter 10.
Dienstag, J. L., et al, Sem Liver Disease, 6:67 (1986)
Feramisco, J. R., et al., J. Biol. Chem. 257(18):11024 (1982).
Gubler, U., et al, Gene, 25:263 (1983).
Hunyh, T. V., et al, in *DNA Cloning Techniques: A Practical Approach* (D. Glover, ed.) IRL Press (1985).
Kuo, G., et al., Science, 244:362 (1989).
Maniatis, T., et al. *Molecular Cloning: A Laboratory Manual*, Cold Spring Harbor Laboratory (1982).
Miller, J. H., *Experiments in Molecular Genetics.*, Cold Spring Harbor Laboratories, Cold Spring Harbor, N.Y. (1972).
Reyes, G., et al, Science, 247:1335 (1990).
Scharf, S. J., et al., Science 233:1076 (1986).
*Selected Method in Cellular Immunology*, (Mishell, B. D., et al. eds) W. H. Freeman and Co., pp416–440 (1980).
Smith. D. B., et al, Gene, 67:31 (1988).
Southern, E., Methods in Enzymology 69:152 (1980).
Woo, S. L. C., Methods in Enzymology 68:389 (1979).
Young, R. A. and R. W. Davis, Proc. Natl. Acad. Sci. USA 80, 1194–1198 (1983).

BACKGROUND

Viral hepatitis resulting from a virus other than hepatitis A virus (HAV) and hepatitis B virus (HBV) has been referred to as non-A, non-B hepatitis (NANBH). More recently, it has become clear that NANBH encompasses at least two, and perhaps more, quite distinct viruses. One of these, known as enterically transmitted NANBH or ET-NANBH, is contracted predominantly in poor-sanitation areas where food and drinking water have been contaminated by fecal matter. The molecular cloning of a portion of this virus, referred to as the hepatitis E virus (HEV), has recently been described (Reyes et al.).

The second NANB virus type, known as parenterally transmitted NANBH, or PT-NANBH, is transmitted by parenteral routes, typically by exposure to blood or blood products. Approximately 10% of transfusions cause PT-NANBH infection, and about half of these go on to a chronic disease state (Dienstag).

Human sera documented as having produced post-transfusion NANBH in human recipients has been used successfully to produce PT-NANBH infection in chimpanzees (Bradley). RNA isolated from infected chimpanzee sera has been used to construct cDNA libraries in an expression vector for immunoscreening with chronic-state human PT-NANBH serum. This procedure identified a PT-NANBH specific cDNA clone and the viral sequence was then used as a probe to identify fragments making up 7,300 contiguous basepairs of a PT-NANBH viral agent (EPO patent application 88310922.5, filed Nov. 18, 1988). The same procedure was used by the present inventors to derive two of the PT-NANBH peptide and polynucleotide sequences disclosed herein. The sequenced viral agent has been named HCV (HCV) (above EPO patent application).

Heretofore, one immunogenic peptide encoded by the HCV viral agent has been reported (Choo, Kuo, EPO application 88310922.5). This peptide, designated C-100, has been used in immunoassays of PT-NANBH sera and found to react immunospecifically with up to 80% of chronic NANBH samples, and about 15% of acute NANBH samples (Kuo).

It is desirable to provide one or a collection of peptide antigens which are immunoreactive with a greater percentage of PT-NANBH-infected blood, including both acute and chronic PT-NANBH infection.

SUMMARY OF THE INVENTION

It is one general object of the invention to provide recombinant polypeptides immunoreactive with sera from humans infected with hepatitis C virus (HCV), including a peptide which is immunoreactive with a high percentage of sera from chronic HCV-infected individuals, and peptides which are immunoreactive with sera associated with acute HCV infection.

It is another object of the invention to provide an HCV polynucleotide sequence encoding a sequence for recombinant production of the peptide antigens, and a diagnostic method for detecting HCV-infected human sera using the peptide antigens.

The invention includes, in one aspect, a peptide antigen which is immunoreactive with sera from humans infected with HCV. One peptide antigen in the invention includes an immunoreactive portion of an HCV polypeptide which:

a) is encoded by an HCV coding sequence;
b) has 504 amino acid residues; and
c) has the carboxy-terminal sequence presented as SEQ ID NO:4.

Other peptide antigens of the invention include an immunoreactive portion of any one of the following sequences: SEQ ID NO:2, SEQ ID NO:8, and SEQ ID NO:10.

In another aspect, the invention includes diagnostic kits for use in screening human blood containing antibodies specific against HCV infection. The kit includes a peptide antigen which is immunoreactive with sera from humans infected with hepatitis C virus (HCV). Four specific peptide antigens for use in the kit are given above.

In one preferred embodiment, the antigen is immobilized on a solid support. The binding of HCV-specific antibodies to the immobilized antigen is detected by a reporter-labeled anti-human antibody which acts to label the solid support with a detectable reporter.

The kit is used in a method for detecting HCV infection in an individual by: (i) reacting serum from an HCV-infected test individual with the above peptide antigen, and (ii) examining the antigen for the presence of bound antibody.

The peptide antigens are produced, in accordance with another aspect of the invention, using an expression system for expressing a recombinant peptide antigen which is immunoreactive with sera from humans infected with hepatitis C virus (HCV). A selected expression vector containing an open reading frame (ORF) of a polynucleotide which encodes the peptide is introduced into a suitable host, which is cultured under conditions which promote expression of the ORF in the expression vector.

In one embodiment, the polynucleotide is inserted into an expression site in a lambda gt11 phage vector, and the vector is introduced into an *E. coli* host. *E coli* hosts and introduced vectors containing the ORF encoding the peptides whose sequences are presented above are identified by ATCC No 40901, ATCC NO. 40893, and ATCC No. 40792, and ATCC No. 40876, respectively. It will be appreciated that determination of other appropriate vector and host combinations for the expression of the above sequences are within the ability of one of ordinary skill in the art.

Also forming part of the invention are polynucleotides which encode polypeptides immunoreactive with sera from humans infected with hepatitis C virus (HCV). One polynucleotide of the present invention encodes a polypeptide wherein the polypeptide includes an immunoreactive portion of a peptide sequence which:
  a) is encoded by an HCV coding sequence;
  b) has 504 amino acid residues; and
  c) has the carboxy-terminal sequence presented as SEQ ID NO:4; and, where the carboxy-terminal amino acid sequence of said peptide antigen is encoded by the polynucleotide sequence presented as SEQ ID NO:3.

Other polynucleotides of the invention include any one of the following sequences: SEQ ID NO:2, SEQ ID NO:8, and SEQ ID NO:10.

These and other objects and features of the invention will become more fully apparent when the following detailed description is read in conjunction with the accompanying drawings.

BRIEF DESCRIPTION OF THE DRAWINGS

FIG. 3 shows the DNA coding sequence of the clone 40 insert. The underlined sequences correspond to an R9 primer region.

FIG. 4 shows the DNA coding sequence of a clone 36 insert. The underlined sequences correspond, respectively, to the F7, F8, and R8 primer regions.

FIG. 5 shows the DNA and protein coding sequences for a 409-1-1(abc) clone insert. The "A" region of this sequence is delineated by boxes, the "B" region by a box and a triangle, and the "C" region by a triangle and an asterisk.

FIGS. 6A and 6B show the DNA and protein coding sequences for a 409-1-1 (c-a) clone insert.

FIGS. 8(A) to 8(H) present a DNA sequence corresponding to the sequence of a genome of an isolate of the Hepatitis C Virus.

DETAILED DESCRIPTION OF THE INVENTION

I. Definitions

Figure 1:
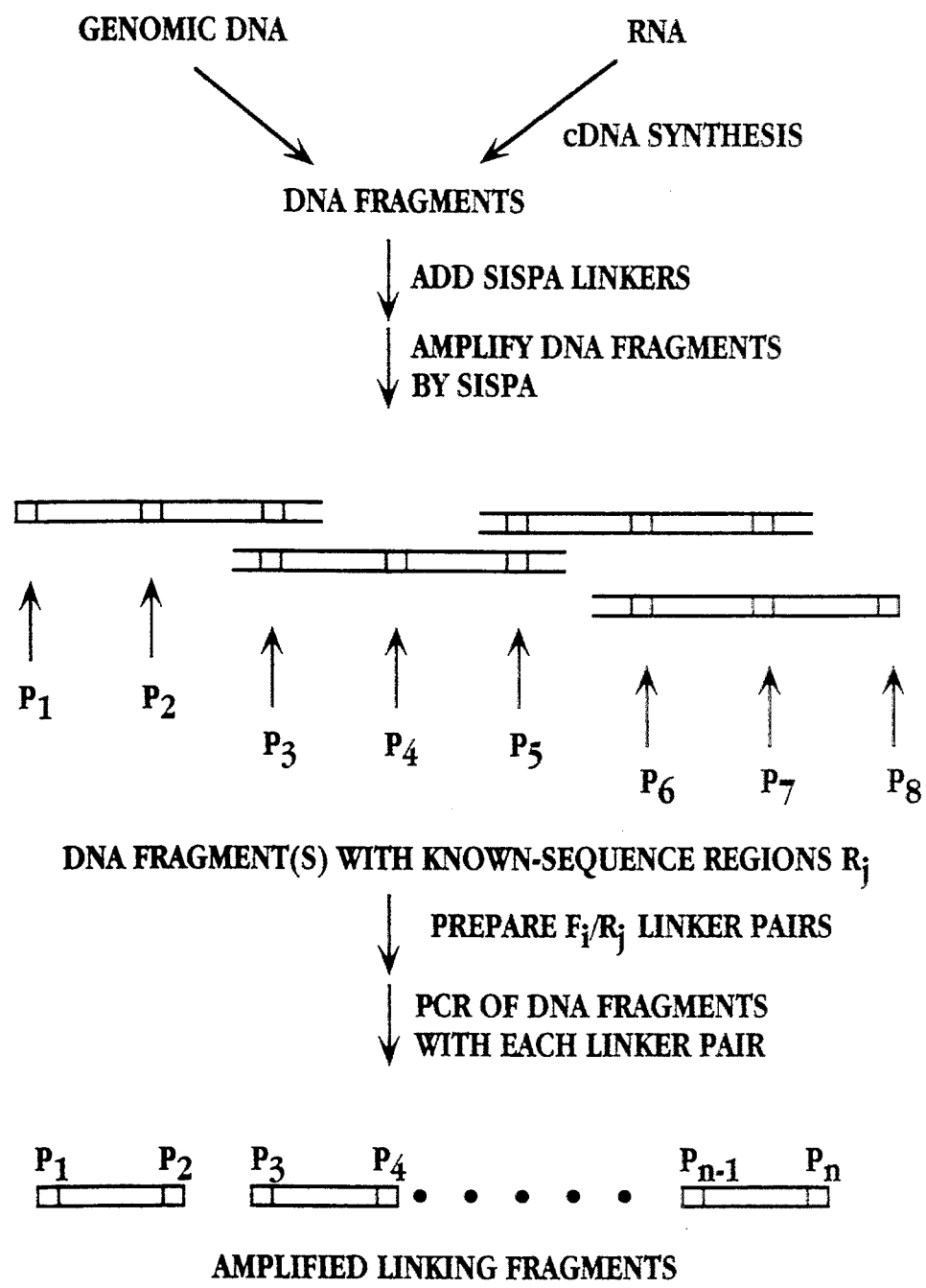
FIG. 1 illustrates the steps in producing overlapping linking fragments of a nucleic acid segment, in accordance with the methods of the present invention.

The terms defined below have the following meaning herein:

1. "Parenterally transmitted non-A, non-B hepatitis viral agent (PT-NANBH)" means a virus, virus type, or virus class which (i) causes parenterally transmitted infectious hepatitis, (ii) is transmissible in chimpanzees, (iii) is serologically distinct from hepatitis A virus (HAV), hepatitis B virus (HBV), and hepatitis E virus (HEV).

2. "HCV (HCV)" means a PT-NANBH viral agent whose polynucleotide sequence includes the sequence of the 7,300 basepair region of HCV given in FIGS. 8(A) to 8(H), and variations of the sequence, such as degenerate codons, or variations which may be present in different isolates or strains of HCV.

3. Two nucleic acid fragments are "homologous" if they are capable of hybridizing to one another under hybridization conditions described in Maniatis et al., op. cit., pp. 320–323, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25-30% basepair mismatches. More preferably, homologous nucleic acid strands contain 15-25% basepair mismatches, even more preferably 5-15% basepair mismatches. These degrees of homology can be selected by using more stringent wash or hybridization conditions for identification of clones from gene libraries (or other sources of genetic material), as is well known in the art.

4. A DNA fragment is "derived from" HCV if it has substantially the same basepair sequence as a region of the HCV viral genome which was defined in (2) above.

5. A protein is "derived from" a PT-NANBH or HCV viral agent if it is encoded by an open reading frame of a cDNA or RNA fragment derived from a PT-NANBH or HCV vital agent, respectively.

II. Molecular Clone Selection by Immunoscreening

As one approach toward identifying a molecular clone of a PT-NANBH agent, cDNA libraries are prepared from infected sera in the expression vector lambda gt11. cDNA sequences are then selected for expression of peptides which are immunoreactive with PT-NANBH-infected sera. Recombinant proteins identified by this approach provide candidates for peptides which can serve as substrates in diagnostic tests. Further, the nucleic acid coding sequences identified by this approach serve as useful hybridization probes for the identification of further PT-NANBH coding sequences.

In order to make immunoscreening a useful approach for identifying clones originating from PT-NANBH coding sequences, a well-defined source of PT-NANBH virus is important. To generate such a source, a chimpanzee (#771; Example 1A) was infected with transmissible PT-NANBH agents using a Factor VIII concentrate as a source (Bradley). The Factor VIII concentrate was known to contain at least two forms of parenterally transmitted NANB hepatitis (PT-NANBH). In addition to a chloroform-sensitive agent, which has subsequently been called HCV (HCV), a chloroformresistant form of PT-NANBH was also transmitted in the concentrate (Bradley, 1983):

In the method illustrated in Example 1, infected serum was pelleted, without dilution, by centrifugation, and cDNA libraries were generated from the resulting pelleted virus (Example 1B and 1C). Sera from infected human sources were treated in the same fashion. cDNA libraries were generated, e.g., by a random primer method using the RNA extracted from pelleted sera as starting material (Example 1B and 1C). The resulting cDNA molecules were then cloned into a suitable vector, for example, lambda gt11, for expression and screening of peptide antigens, and lambda gt10, for hybridization screening (Example 1C(iv)). Lambda gt11 is a particularly useful expression vector which contains a unique EcoRI insertion site 53 base pairs upstream of the translation termination codon of the beta-galactosidase gene. Thus, an inserted sequence is expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant clone generation, (2) ability to select lysogenized host cells on the basis of host-cell growth at permissive, but not non-permissive, temperatures, and (3) high levels of recombinant fusion protein production. Further, since phage containing a heterologous insert produces an inactive beta-galactosidase enzyme, phage with inserts are typically identified using a beta-galactosidase colored-substrate reaction.

In the screening procedure reported in Examples 1–3, individual cDNA libraries were prepared from the serum of one PT-NANBH infeced chimpanzee (#771) and four PT-NANBH infected humans (designated EGM, BV, WEH, and AG). These five libraries were immunoscreened using PT-NANBH positive human or chimpanzee sera (Example 2): 111 lambda gt11 clones were identified which were immunoreactive with at least one of the sera. Of these 111 clones, 93 were examined for insert hybridization with normal DNA. The inserts were radioactively labelled and used as probes against HindIII/EcoRI doubly-digested human peripheral lymphocyte (PBL) DNA (Example 3). Approximately 46% (43/93) of the inserts hybridized with normal human PBL DNA and were therefore not pursued. Inserts from 11 PT-NANBH-immunopositive clones derived from chimpanzee #771 sera were characterized as exogenous to normal human PBL DNA (Example 3). Of these 11 clones 2 PT-NANBH clones were identified having the following characteristics. One clone (clone 40) was clearly exogenous by repeated hybridization tests against normal human PBL DNA, had a relatively small insert size (approximately 0.5 kilobases), and was quite unreactive with negative control serum. The second clone (clone 36) was shown to be reactive with multiple PT-NANBH antisera, had a relatively large insert size (approximately 1.5 kilobases), and was exogenous by hybridization testing against normal human PBL DNA. The immunoreactive characteristics of clones 36 and 40 are summarized in Table 1 (Example 3). Clone 36 was immunoreactive with chimpanzee #771 sera and two HCV-positive human sera, AG and BV. The clone 36 antigen did not immunoreact with the negative control sera SKF. Clone 40 was immunoreactive with chimpanzee #771 sera and was cleanly nonreactive when the negative control sera was used for screening.

The DNA sequence of clone 36 was determined in part and is shown in FIG. 4. This sequence corresponds to nucleotides 5010 to 6516 of the HCV sequence given in FIGS. 8(A) to 8(H). The DNA sequence was also determined for the clone 40 insert (FIG. 3). This sequence is homologous to the HCV sequence (FIGS. 8(A) to 8(H)) in the region of approximately nucleotides 6515 to 7070. The inserts of two other chimpanzee #771 clones, clones 44 and 45, were found to be homologous to clone 40 by hybridization and sequence analysis (Example 4). The sequences for clones 36 and 40 are contiguous sequences, with the clone 36 sequences being located 5' of the clone 40 sequences as presented in FIGS. 8(A) to 8(H). Accordingly, these two clones represent isolation of a significant block of the HCV genome by the above-described immunoscreening methods.

The four lambda gt11 clones 36, 40, 44, and 45 were deposited in the Genelabs Culture Collection, Genelabs Incorporated, 505 Penobscot Drive, Redwood City, Calif. 94063. Further, the lambda gt11 clones of clones 36 and 40 were deposited with the American Type Culture Collection, 12301 Parklawn Dr., Rockville Md., 20852, and given the deposit numbers ATCC No. 40901 and ATCC 40893.

III. PT-NANBH Sequence Identification by Hybridization Methods.

The polynucleotides identified in Section II can be employed as probes in hybridization methods to identify further HCV sequences, and these can then be used as probes to identify additional sequences. The polynucleotides can be directly cloned or fragmented by partial digestion to generate random fragments. The resulting clones can be immunoscreened as described above to identify HCV antigen coding sequences.

To illustrate how the inserts of clones 36 and 40 can be used to identify clones carrying HCV sequences, the insert of clone 40 was isolated and used as a hybridization probe against the individual cDNA libraries established in lambda gt10 (see above). Using the clone 40 probe approximately 24 independent hybridization-positive clones were plaque purified (Example 5). The positive signals arose with different frequencies in cDNA libraries from the different serum sources, suggesting that the hybridization signals were from the serum sources, rather than resulting from some common contaminant introduced during the cDNA synthesis or cloning (Table 2). One of the clones, 108-2-5, which tested positive by hybridization with the clone 40 insert, had an insert of approximately 3.7 kb (Example 6). Since it had such a large insert, clone 108-2-5 was chosen for further analysis. The serum source of this cDNA clone was EGM human PT-NANBH serum (Example 1).

The insert of 108-2-5 was isolated by EcoRI digestion of the lambda gt10 clone, electrophoretic fractionation, and electroelution (Example 6). The isolated insert was treated with DNase I to generate random fragments (Example 6), and the resulting digest fragments were inserted into lambda gt11 phage vectors for immunoscreening. The lambda gt11 clones of the 108-2-5 fragments were immunoscreened (Example 6) using human (BV and normal) and chimpanzee #771 serum. Twelve positive clones were identified by first round immunoscreening with the human and chimp sera. Seven of the 12 clones were plaque purified and rescreened using chimpanzee #771 serum. Partial DNA sequences of the insert DNA were determined for two of the resulting clones, designated 328-16-1 and 328-16-2. These two clones contained sequences essentially identical to clone 40 (Example 6).

The clone 36 insert can be used in a similar manner to probe the original cDNA library generated in lambda gt10. Specific subfragments of clone 36 may be isolated by Polymerase chain reaction or after cleavage with restriction endonucleases. These fragments can be radioactively labelled and used as probes against the cDNA libraries generated in lambda gt10 (Example 1C). In particular, the 5' terminal sequences of the clone 36 insert are useful as probes to identify clones overlapping this region.

Further, the sequences provided by the terminal clone 36 insert sequences and the terminal clone 40 insert sequences are useful as specific sequence primers in first-strand DNA synthesis reactions (Maniatis et al.; Scharf et al.) using, for example, chimpanzee #771 sera generated RNA as substrate. Synthesis of the second-strand of the cDNA is randomly primed. The above procedures identify or produce cDNA molecules corresponding to nucleic acid regions that are 5' adjacent to the known clone 36 and 40 insert sequences. These newly isolated sequences can in turn be used to identify further flanking sequences, and so on, to identify the sequences composing the HCV genome. As described above, after new HCV sequences are isolated, the polynucleotides can be cloned and immunoscreened to identify specific sequences encoding HCV antigens.

IV. Generating Overlapping Cloned Linking Fragments

This section describes a method for producing and identifying HCV peptides which may be useful as HCV-diagnostic antigens. The present method is used to generate a series of overlapping linking fragments which span a segment of nucleic acid. The application of the method to generating a series of overlapping linking fragments which span a 7,300 basepair segment of the HCV genome, whose sequence is given in FIGS. 8(A) to 8(H), will be described with reference to FIGS. 1 and 2.

As a first step in the method, and with reference to FIG. 1, the nucleic acid of interest is obtained in double-strand DNA form. Typically, this is done by isolating genomic DNA fragments or by producing cDNAs from RNA species present in a sample fluid. The latter method is used to generate double-strand DNA from NANBH viral RNA present in serum from chimpanzees or humans with known PT-NANBH infection. Here RNA in the sample is isolated, e.g., by guanidinium thiocyanate extraction of PEG precipitated virions, and reacted with a suitable primer for first strand cDNA synthesis.

First-strand cDNA priming may be by random primers, oligo dT primers, or sequence-specific primer(s). The primer conditions are selected to (a) optimize generation of cDNA fragments which collectively will span the nucleic acid segment of interest, and (b) produce cDNA fragments which are preferably equal to or greater than about 1,000 basepairs in length. In one method applied to HCV RNA, the first-strand synthesis is carried out using sequence-specific primers which are complementary to spaced regions along the length of the known HCV genomic sequence. The primer position are indicated at A, B, C, and D in FIG. 2, which shows a map of the HCV genome segment. The basepair locations of the primers in the HCV genome are given in Example 7 below. Following first strand synthesis, the second cDNA strand is synthesized by standard methods.

The linking fragments in the method are produced by sequence-specific amplification of the double-strand DNA obtained as above, using pairs of overlap-region primers to be described. According to an important advantage of the methods of the present invention, it is possible to generate linking fragments even when the amount of double-strand DNA is too low for direct sequence-specific amplification. This limitation was found, for example, with HCV cDNA's produced from NANBH-infected serum. Here the amount of double-stranded DNA available for amplification is first amplified nonspecifically by a technique known as Sequence-Independent Single-Primer Amplification (SISPA).

The SISPA technique is detailed in co-owned U.S. Patent application for "RNA and DNA Amplification Techniques", Ser. No. 224,961, filed Jul. 26, 1988. The method as applied to amplification of HCV cDNA fragments is also described in Example 7. Briefly, known-sequence linker primers are attached to opposite ends of double-stranded DNA in a DNA sample. These linkers then provide the common end sequences for primer-initiated amplification, using primers complementary to the linker/primer sequences. Typically, the SISPA method is carried out for 20–30 cycles of amplification, using thermal cycling to achieve successive denaturation and primer-initiated polymerization of second strand DNA.

FIG. 1 illustrates the SISPA amplification of duplex DNA, to form amplified fragments which have known-sequence regions $P_i$. As seen, the fragment mixture includes at least some fragments which (a) overlap at regions $P_i$ with other fragments in the mixture and (b) contain complete linking regions between adjacent $P_i$ and $P_{i+1}$ regions. Collectively, each linking region bounded by the associated overlap regions making up the segment is present in at least one DNA fragment.

Figure 2:
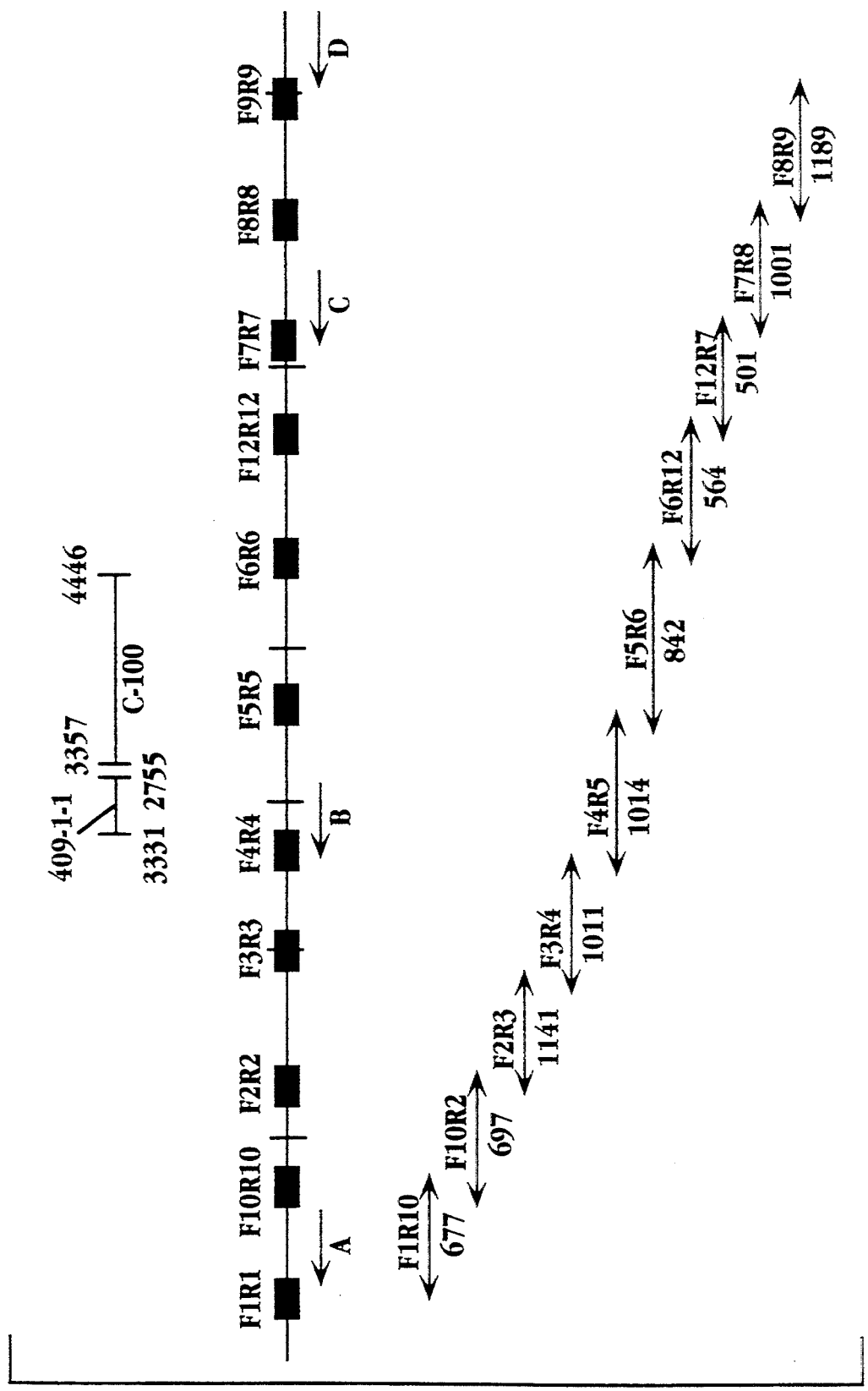
FIG. 2 shows the positions of overlap primer regions and linking regions along a 7,300 basepair portion of the HCV genome.

The production of overlapping linking fragments, in accordance with the methods of the present invention, is carried out using the polymerase chain reaction (PCR) method described in U.S. Pat. No. 4,683,195. In practicing this step of the method, first the total segment of interest is divided into a series of overlapping intervals bounded by regions of known sequence, as just described. In FIG. 2, the 7,300 basepair segment of the HCV genome has been divided into 10 intervals, each about 500–1,000 basepairs in length. The intervals are designated according to the forward $F_i$ and reverse $R_j$ primers used in amplifying the sequence, as will be described. The selection of the intervals is guided by (a) the requirement that the basepair sequence at each end of the interval be known, and (b) a preferred interval length of between about 500 and 2,000 basepairs.

In the method applied to the 7,300 basepair segment of the HCV genome, the regions of overlap between the ten intervals were additionally amplified, to verify that the SISPA-amplified cDNA sample contained sufficient HCV cDNA to observe PCR-amplification of HCV linking fragments, and that HCV regions along the entire length of the genome were available for amplification. Each overlap region in the segment can be defined by a pair of primers which includes a forward primer $F_i$ and a reverse primer $R_i$ which are complementary to opposite strands of opposite ends of the overlap region. The primers are typically about 20 basepairs in length and span an overlap region of about 200 basepairs. The eleven overlap regions in the HCV segment and the regions corresponding to the forward and reverse primers in each region are given in Example 8.

The primers $F_i/R_i$ are added to the amplified DNA material in a PCR reaction mix, and the overlap region bounded by the primers is amplified by 20–30 thermal cycles. The reaction material is then fractionated, e.g., by agarose gel electrophoresis, and probed for the presence of the desired sequence, e.g., by Southern blotting (Southern), using a radiolabeled oligonucleotide probe which is specific for an internal portion of the overlap region. As described in Example 8, this method was successful in producing amplified fragments for each of the eleven $F_i/R_i$ overlap regions in the HCV genome segment. The overlap-region fragments may be used as probes for the corresponding (two) linking fragments connected by the overlap region. It is emphasized, however, that this amplification step was employed to confirm the presence of amplifiable cDNA along the length of the HCV genome, and not as an essential step in producing the desired linking fragments. The step is omitted from FIG. 1.

The linking fragments $F_i/R_j$ are produced by a two-primer PCR procedure in which the SISPA-amplified DNA fragments are amplified by a primer pair consisting of the forward primer $F_i$ of one overlap region and the reverse primer $R_j$ of an adjacent overlap region. The ten overlap regions in the HCV segment and the regions corresponding to the forward and reverse primers in each region are given in Example 9. Typical amplification conditions are give in Example 9. The amplified fragments in each reaction mixture are isolated and purified, e.g., by gel electrophoresis, to confirm the expected fragment size. Southern blots may be probed with oligonucleotide probes complementary to internal regions located between the fragment ends, to confirm the expected sequence of the fragments. As shown at the bottom in FIG. 1, the method generates the complete set of linking fragments, where each fragment is bounded by an overlap region $P_i$ and $P_{i+1}$.

The method, as applied to generating ten overlapping linking fragments of the 7,300 basepair HCV genome, is described in Example 9. As demonstrated by size criteria on gel electrophoresis and by sequence criteria by Southern blotting, the method was successful in generating all ten of the overlapping fragments spanning the HCV genome.

It will be appreciated that the above flanking sequence amplification method can be applied to the generation of DNA fragments corresponding to the insert sequences of clones 36 and 40, which have also been obtained by immunoscreening. The linker primers flanking the inserts are easily used to generate sequences corresponding to the clone inserts. For example, two-primer amplification of the SISPA-amplified cDNA fragments (Example 7) using the $F_{12}/R_9$ primer pair (the sequences of which are given in Example 8) is carried out under conditions similar to those described in Example 9. The amplified fragment mixture is fractionated by agarose electrophoresis on 1.0% agarose, and the expected band cut from the gel and eluted.

The purified amplified fragment is treated with the Klenow fragment of DNA polymerase I to assure the molecules are blunt-ended. The fragment is then ligated to EcoRI linkers (Example 10). The mixture is digested with EcoRI and inserted into the lambda gt11 vector. The resulting clones contain the entire coding sequences of either the clone 36 or clone 40 inserts.

Alternatively, the original amplified 36/40 fragment (primers $F_{12}/R_9$) is briefly treated with Exonuclease III (Boehringer Mannheim, as per manufacturer's instructions) to generate a family of fragments with different 5' ends. The digestion products are treated as above and ligated into the lambda gt11 vector. The resulting plaques are then immunoscreened.

Further, different sets of primers, other than the $F_{12}/P_9$ primers described above, can be used to directly generate sequence encoding all, or portions, of clones 36 and 40. For example, primers $F_8/R_9$ can generate a fragment corresponding to a portion of the 3' sequences of the insert of clone 36 (FIG. 4) and all of the insert sequences of clone 40 (FIG. 3). Also, primers $F_7/R_8$ can be used to directly generate a fragment corresponding to a portion of the 5' sequences present in the insert of clone 36 (FIG. 4).

V. PT-NANBH Immunoreactive Peptide Fragments

Several novel peptide antigens which are immunoreactive with sera from human and chimpanzee NANBH-infected sera have been generated from the NANBH linking fragments produced above, in accordance with the methods of the present invention. Further, this method has confirmed antigenic regions previously identified by cDNA library immunoscreening (Section II above). The antigen peptides derived from linking fragments are preferably produced in a method which involves first digesting each of the above linking fragments with DNaseI under partial digestion conditions, yielding DNA digest fragments predominantly in the 100–300 basepair size range, as illustrated in Example 10. The digest fragments may be size fractionated, for example by gel electrophoresis, to select those in the desired size range.

The digest fragments from each linking fragment are then inserted into a suitable expression vector. One exemplary expression vector is lambda gt11, the advantages of which have been described above.

For insertion into the expression vector, the digest fragments may be modified, if needed, to contain selected restriction-site linkers, such as EcoRI linkers, according to conventional procedures. Typically, the digest fragments are blunt-ended, ligated with EcoRI linkers, and introduced into EcoRI-cut lambda gt11. Such recombinant techniques are well known in the art (e.g., Manjarls et al.).

The resulting viral genomic library may be checked to confirm that a relatively large (representative) library has been produced for each linking fragment. This can be done, in the case of the lambda gt11 vector, by infecting a suitable bacterial host, plating the bacteria, and examining the plaques for loss of beta-galactosidase activity, as evidenced by clear plaques.

The presence of a digest-fragment insert in the clear plaques can be confirmed by amplifying the phage DNA, using primers specific for the regions of the gt11 phage flanking the EcoRI insert site, as described in Example 10B. The results in Table 3 show that a large percentage of the plaques tested in each linking fragment library contained a digest-fragment insert.

The linking-fragment libraries may also be screened for peptide antigens which are immunoreactive with human or chimpanzee sera identified with PT-NANBH chronic, convalescent, or acute infection. One preferred immunoscreening method is described in Example 10B. Here recombinant protein produced by the phage-infected bacteria is transferred from the plaques to the filter. After washing, the filter is incubated with test serum, and then reacted with reporter-labeled anti-human IgG antibody. The presence of the peptide antigen on the filter is then assayed for the presence of the reporter. As seen from Table 3, several of the linking-fragment libraries were positive for immunoreactive peptides in the primary screen.

The immunoscreening method just described can be used to identify library plaques from each of the linking libraries which are immunoreactive with sera from human or chimpanzee with known chronic, convalescent, or acute PT-NANBH infection. One exemplary screening procedure is given in Example 11, where the ten HCV linking-fragment libraries are screened with known PT-NANBH (a) human chronic serum, (b) chimpanzee acute pooled sera and (c) chimpanzee chronic pooled sera. Of the ten libraries examined, only the $F_1/R_{10}$ library did not give positive immunoreaction with any of the three sera. Several of the fragment libraries, including $F_3/R_4$, $F_6/R_{12}$, $F_{12}/R_7$, and $F_7/R_8$ showed five or more positive reactions with chimpanzee acute sera, indicating that these libraries each express one or more peptide antigens which are useful for detecting chimapanzee or human acute PT-NANBH infection.

The fragment library $F_7/R_8$ corresponds to an internal fragment of clone 36 insert (Section II; FIG. 4). Accordingly, the linking fragment method confirmed that this DNA region encodes a useful antigen. Further, the fragment library $F_8/R_9$ contains the sequences present in the clone 40 insert (Section II: FIGS. 3 and 4). The results in Table 4 indicate that at least one peptide antigen effective to detect the presence of chronicinfection serum was isolated from the $F_8/R_9$ fragment library.

VI. Immunoreactive 409-1-1 Peptides

A. Immunoreactive Screening

Two of the immunoreactive plaques identified by immunoreactive screening, designated 409-1-1(abc) and 409-1-1(c-a), were tested for immunoreactivity against well-documented PT-NANBH chronic sera which showed strong immunoreactivity to the 5-1-1 HCV peptide antigen (Kuo). The 5-1-1 HCV peptide antigen has previously been identified as immunoreactive against a high percentage of human PT-NANBH chronic sera. The 5-1-1 antigen is encoded by the sequence between basepairs 3731 and 3857 in the HCV genome (FIGS. 8(A) to 8(H)) and is itself contained in a larger peptide antigen C-100 encoded by the sequence between basepairs 3531 and 4442. The latter peptide is employed in a commercial diagnostic kit for detection of human HCV infection (Ortho/Chiron). The kit is reported to react positively with about 80% of human chronic PT-NANBH samples, and about 15% of human acute PT-NANBH sera, as noted above.

The 409-1-1 (c-a) phage was identified by immunoscreening and plaque purified, as outlined above. A related clone, designated 409-1-1(abc), was described in the parent to the present application (U.S. application Ser. No. 07/505,611, herein incorporated by reference). Clone 409-1-1(abc) was designated 409-1-1 in the parent application. The a, b and c designations refer to three regions of the 409-1-1(abc) sequence (see FIG. 5). The 5-1-1 coding sequence was isolated by polymerase chain reaction using oligonucleotide primers complementary to the ends of the 5-1-1 coding region, and cloned into lambda gt11 for expression under induction conditions of a fused beta-galactosidase protein which includes the 5-1-1 antigen peptide region. The 5-1-1 phage was identified and plaque purified by similar methods.

The 409-1-1(c-a) and 5-1-1 antigens were compared by plaque immunoscreening with a panel of 28 sera from normal (2 donors), human PT-NANBH-chronic (6 donors), chimpanzee normal (7 donors), chimpanzee PT-NANBH-acute (5 donors), and chimpanzee PT-NANBH-chronic (8 donors), with the results shown in Table 5 in Example 12. As can be seen in Table 5, the 5-1-1 and 409-1-1(c-a) peptides reacted with most of the human and chimpanzee chronic sera, although the 409-1-1(c-a) peptide detected a higher percentage of human chronic sera samples (83% vs 66%). The chronic human serum which was detected by the 409-1-1(c-a) peptide, but not by 5-1-1 was from a patient (BV) who died of fulminant NANBH infection. Because the 5-1-1 antigen is contained within the C-100 antigen in the commercially available kit format (Ortho/Chiron), it was of interest to determine whether the C-100 antigen gave a broader range of reactivity with the test sera. The results are shown at the right in Table 5 below. The only human NANBH serum that was tested was the above BV serum which was not detected by 5-1-1. This serum was also not immunoreactive with the C-100 antigen (0/1). Nor was the C-100 antigen reactive with any of the five acute chimp sera which were tested (0/5). It is also noted that the 409-1-1(c-a) antigen is immunoreactive with 3 of the 5 acute chimpanzee sera tested, compared with only 1 out of 5 for the 5-1-1 antigen. The results indicate that the 409-1-1(c-a) antigen has broader immunospecificity with PT-NANBH sera, and thus would provide a superior diagnostic agent. The results obtained with 409-1-1(c-a) are comparable to the results obtained using 409-1-1(abc).

It is noted here that the 409-1-1(abc) coding sequence is contained in the $F_4/R_5$ linking fragment and does not overlap the sequence of the C-100 (and 5-1-1) coding region which is in the $F_4/R_5$ and $F_5/R_6$ linking fragments. The relatively long coding sequence of the 409-1-1(abc) peptide illustrates that larger size digest fragments (substantially greater than 300 basepairs) are generated in the partial digest step used in producing digest fragments for antigen expression.

The 409-1-1(abc) peptide, which forms one aspect of the invention, has the amino acid sequence which is presented as SEQ ID NO:10. The DNA coding sequence corresponding to the insert in the 409-1-1 clone is given in FIG. 5 and is presented as SEQ ID NO:9.

The 409-1-1(c-a) peptide, which forms another aspect of the invention, has the amino acid sequence presented as SEQ ID NO:8. The DNA coding sequence corresponding to the insert in the 409-1-1(c-a) clone is given in FIGS. 6A and 6B and is presented as SEQ ID NO:7. The relationship between the coding sequence of 409-1-1(c-a) and 409-1-1(abc) is outlined in Example 12. Briefly, 409-1-1(c-a) consists of a carboxy terminal region of 409-1-1(abc) moved to the amino terminus of the 409-1-1 coding sequence, with a truncation of the remaining 3' 409-1-1(abc) coding sequence.

More generally, the invention includes a peptide antigen which is immunoreactive with sera from humans with HCV infection. Such peptide antigens are readily identifiable by the methods of the present invention.

Figure 7:
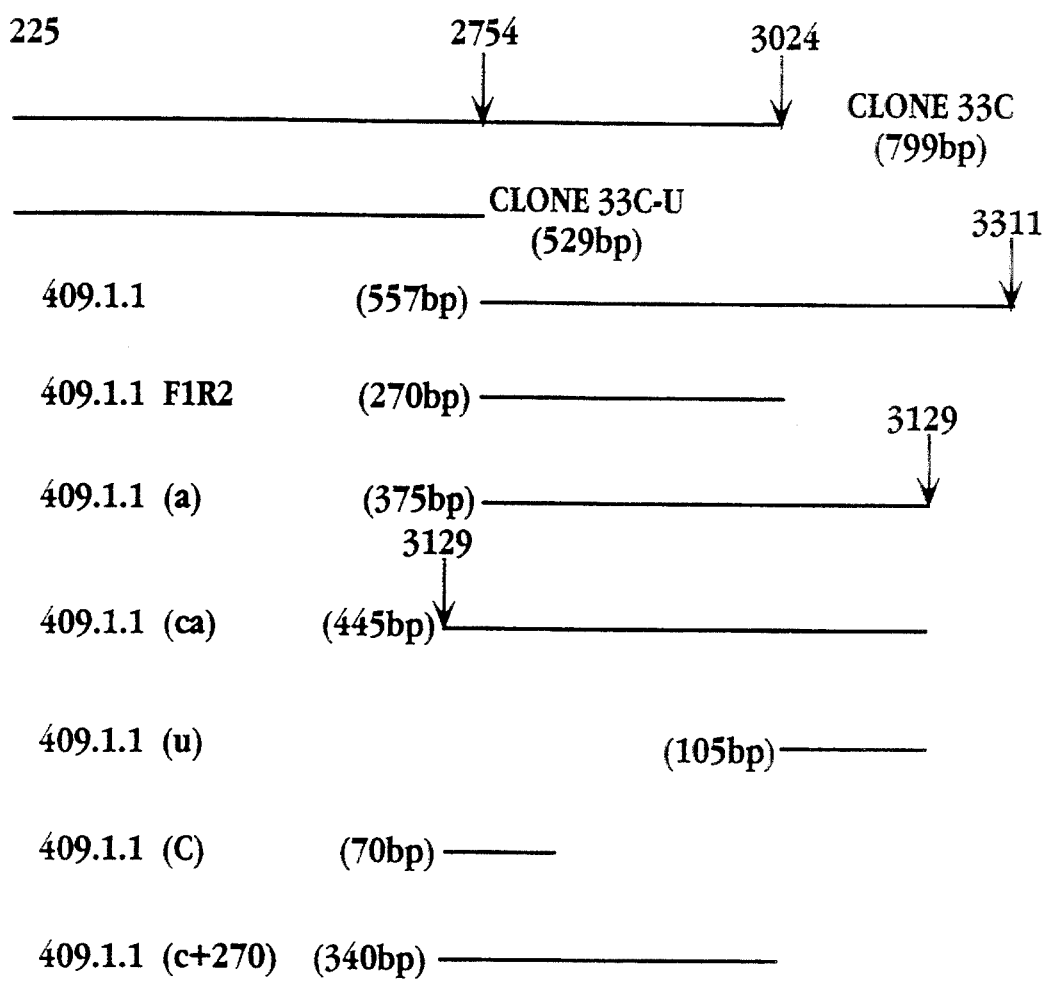
FIG. 7 illustrates the groups of clones which have been obtained from the HCV genome in the region corresponding to the 409-1-1 (abc) clone insert.

Antigens obtained from the region corresponding to the HCV sequences encoding the 409-1-1 antigens were further characterized as follows. The primers shown in Table 7 were used to generate a family of overlapping amplified fragments derived from this region. Several templates were used for the DNA amplification reactions (Table 8). The relationships of the coding sequences of the resulting clones to each other are graphically illustrated in FIG. 7. The amplified fragments were then cloned into lambda gt11 vectors (Example 13).

These cloned fragments were then immunoscreened (Example 13). Seven of the nine clones tested positive by preliminary immunoscreening (Table 9). These seven clones were then tested against a more extensive battery of PT-NANBH serum sample including numerous human clinical samples. The sensitivity of the antigens, in decreasing order, for reactivity with the serum used for screening was as follows: 33cu>33c>409-1-1(c-a)>409-1-1-F1R2>409-1-1(abc)≈409-1-1a>5-1-1>409-1-1(c+270). As can be seen from these results all of the alternative clones, with the exception of 409-1-1(c+270), provided a more sensitive antigen than 5-1-1. However, although 33cu and 33c were very sensitive antigens, in this assay they reacted slightly with serum which was known to be negative for HCV and may therefore be less specific. Accordingly, the 409-1-1 series appears preferable for use as diagnostic antigens since they are more specific to HCV-induced antibodies.

The immunoscreening was extended to include the clone 36 and 45 encoded epitopes: the insert of clone 45 is essentially the same as the insert of clone 40 (Example 4). As can be seen from the results presented in Table 11, the antigens produced by clones 36 and 40, while not as sensitive as 409-1-1(c-a), do yield HCV-specific immunopositive signals with selected samples. Accordingly, the two methods presented in the present invention, (i) immunoscreening of cDNA libraries generated directly from sera-derived RNA, and (ii) immunoscreening of amplified-fragment libraries, can both be seen to be effective methods of identifying cDNA sequences encoding viral antigens. Further, confirmation of the clone 36 and 40 encoded antigens by identification of antigens corresponding to these HCV regions using the amplified-fragment library method validates the usefulness of the amplified-fragment method.

B. Peptide Purification

The recombinant peptides of the present invention can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused proteins prepared as above, the fused protein can be isolated readily by affinity chromatography, by passing cell lysis material over a solid support having surface-bound anti-beta-galactosidase antibody. For example, purification of a beta-galactosidase/fusion protein, derived from 409-1-1(c-a) coding sequences, by affinity chromatography is described in Example 14.

A fused protein containing the 409-1-1(a) peptide fused with glutathione-S-transferase (Sj26) protein has also been expressed using the pGEX vector system in *E. coli* KM392 cells (Smith). This expression system has the advantage that the fused protein is generally soluble and therefore can be isolated under non-denaturing conditions. The fused Sj26 protein can be isolated readily by glutathione substrate affinity chromatography (Smith). This method of expressing this fusion protein is given in Example 15 and is applicable to any of the other antigen coding sequences described by the present invention.

Also included in the invention is an expression vector, such as the lambda gt11 or pGEX vectors described above, containing the 409-1-1(a) coding sequence and expression control elements which allow expression of the coding region in a suitable host. The coding sequence is contained in the sequence given above corresponding to basepairs 2755-3331 of the HCV genome. The control elements generally include a promoter, translation initiation codon, and translation and transcription termination sequences, and an insertion site for introducing the insert into the vector. In the case of the two vectors illustrated in Example 15, the control elements control the synthesis of the protein which is fused with the heterologous peptide antigen. Such expression vectors can be readily constructed for the other antigen coding sequences described by the present invention.

The lambda gt11 vectors containing the following coding regions have been deposited with The American Type Culture Collection, 12301 Parklawn Dr., Rockville Md., 20852: the 409-1-1(abc) coding region, designated gt11/409-1-1(abc), ATCC No. 40876; the 409-1-1(c-a) coding region, designated gt11/409-1-1(c-a) ATCC No. 40792; clone 36, designated gt11/36, ATCC No. 40901; and, clone 40, designated gt11/40, ATCC No. 40893.

VII. Anti-HCV Antigen Antibodies

In another aspect, the invention includes antibodies specific against the recombinant antigens of the present invention. Typically, to prepare antibodies, a host animal, such as a rabbit, is immunized with the purified antigen or fused protein antigen. The host serum or plasma is collected following an appropriate time interval, and this serum is tested for antibodies specific against the antigen. Example 15 describes the production of rabbit serum antibodies which are specific against the 409-1-1 antigens in the Sj26/409-1-1(a) and beta-galactosidase/409-1-1(c-a) fusion protein. These techniques are equally applicable to the other antigens of the present invention.

The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, the purified antigen or fused antigen protein may be used for producing monoclonal antibodies. Here the spleen or lymphocytes from an immunized animal are removed and immortalized or used to prepare hybridomas by methods known to those skilled in the art. To produce a human-human hybridoma, a human lymphocyte donor is selected. A donor known to be infected with an HCV virus (where infection has been shown for example by the presence of anti-virus antibodies in the blood) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity, for example, using the Western blot method described in Example 15.

VIII. Utility

A. Diagnostic Method and Kit

The antigens obtained by the methods of the present invention are advantageous for use as diagnostic agents for anti-HCV antibodies present in HCV-infected sera; particularly, the 409-1-1 antigens (409-1-1(abc), 409-1-1(c-a), and related antigens, see Table 9); the clone 36 antigen; and, the clone 40 antigen. As noted above, many of the antigens provide the advantage over known HCV antigen reagents 5-1-1 and C-100 in that they are immunoreactive with a wider range of PT-NANBH infected sera, particularly acute-infection sera.

In one preferred diagnostic configuration, test serum is reacted with a solid phase reagent having a surface-bound HCV antigen obtained by the methods of the present invention, e.g., the 409-1-1(c-a) antigen. After binding anti-HCV antibody to the reagent and removing unbound serum components by washing, the reagent is reacted with reporter-labeled anti-human antibody to bind reporter to the reagent in proportion to the amount of bound anti-PT-NANBH antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined, either IgM (acute phase) or IgG (convalescent or chronic phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant HCV antigen (e.g., the 409-1-1 antigens, etc., as above), and a reporter labeled reporter-labeled anti-human antibody for detecting surface-bound anti-PT-NANBH-antigen antibody.

As discussed in Section III above, peptide antigens associated with several of the linking-fragment libraries are immunoreactive with acute NANBH sera from chimpanzees, indicating that the peptides would be useful for detecting acute NANBH infection in human serum. In particular, one or more peptide antigens produced by the linking fragment libraries, $F_8/R_9$ (reactive with chronic sera), $F_3R_4$, $F_{12}R_7$, $F_7R_8$, or $F_7R_8$ (which are shown in Example 11 to produce one or more peptide antigens which are immunoreactive with acute chimpanzee sera) can be combined with the 409-1-1 antigens to provide a diagnostic composition capable of immunoreacting with a high percentage of both chronic and acute human NANBH serum samples.

A third diagnostic configuration involves use of the anti-HCV antibodies, described in Section V above, capable of detecting HCV specific antigens. The HCV antigens may be detected, for example, using an antigen capture assay where HCV antigens present in candidate serum samples are reacted with an HCV specific monoclonal antibody. The monoclonal antibody is bound to a solid substrate and the antigen is then detected by a second, different labelled anti-HCV antibody: the monoclonal antibodies of the present invention which are directed against HCV specific antigens are particularly suited to this diagnostic method.

B. Peptide Vaccine

The HCV antigens identified by the methods of the present invention, e.g. 409-1-1(c-a), can be formulated for use in a HCV vaccine. The vaccine can be formulated by standard methods, for example, in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

A specific example of a vaccine composition includes, in a pharmacologically acceptable adjuvant, a recombinant 409-1-1(c-a) peptide. The vaccine is administered at periodic intervals until a significant titer of anti-HCV antibody is detected in the serum.

C. Passive Immunoprophylaxis

The anti-HCV antibodies of the invention can be used as a means of enhancing an anti-HCV immune response since antibody-virus complexes are recognized by macrophages and other effector cells. The antibodies can be administered in amounts similar to those used for other therapeutic administrations of antibody. For example, pooled gamma globulin is administered at 0.02–0.1 ml/lb body weight during the early incubation of other vital diseases such as rabies, measles and hepatitis B to interfere with viral entry into cells. Thus, antibodies reactive with, for example, the 409-1-1(c-a) antigen can be passively administered alone in a "cocktail" with other anti-viral antibodies or in conjunction with another anti-viral agent to a host infected with an PT-NANBH virus to enhance the immune response and/or the effectiveness of an antiviral drug.

The following examples illustrate various aspects of the invention, but are in no way intended to limit the scope thereof.

Materials

*E. coli* DNA polymerase I (Klenow fragment) was obtained from Boehringer Mannheim Biochemicals (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Example 1

Construction of NANB-containing cDNA libraries

A. Infection of a Chimpanzee with HCV

A chimpanzee (#771) was inoculated with a Factor VIII preparation which was known to cause parenterally transmitted non-A non-B hepatitis (PT-NANBH) in human patients treated with the Factor VIII concentrate (Bradley). Post-infection ultrastructural changes in liver tissue were observed by electron microscopy and ALT (alanine amino transferase) elevation was observed in the infected chimpanzee. These observations are consistent with PT-NANBH infection.

B. Isolation of RNA from Sera

Serum was collected from the above described infected chimpanzee (#771) and four human PT-NANBH clinical sources (EGM, BV, CC and WEH). Ten milliliters of each undiluted serum was pelleted by centrifugation at 30K, for 3 hours in an SW40 rotor, at 4° C. RNA was extracted from each resulting serum pellet using the following modifications of the hot phenol method of Feramisco et al. Briefly, for each individual serum sample, the pellet was resuspended in 0.5 ml of 50 mM NaOAc, pH=4.8, containing 1% SDS. An equal volume of 60° C. phenol was added and incubated for 15 minutes at 60° C. with occasional vortexing. This mixture was transferred to a 1.5 ml microfuge tube and spun for two minutes at room temperature in a table top microfuge. The aqueous phase was transferred to a new microfuge tube. To the aqueous phase, 50 µl of 3M NaOAc, pH=5.2, and two volumes of 100% ethanol were added. This solution was held at −70° C. for approximately 10 minutes and then spun in a microfuge at 4° C. for 10 minutes. The resulting pellet was resuspended in 100 µl of sterile glass distilled water. To this solution 10 µl of NaOAc, pH=5.2, and two volumes of 100% ethanol were added. The solution was held at −70° C. for at least 10 minutes. The RNA pellet was recovered by centrifugation in a microfuge at 12,000×g for 15 minutes at 5° C. The pellet was washed in 70% ethanol and dried under vacuum.

C. Synthesis of cDNA

(i) First Strand Synthesis

The synthesis of cDNA molecules was accomplished as follows. The above described PaPA preparations were each resuspended in 26 µl of sterile glass distilled water (treated with diethyl pyrocarbonate, Maniatis et al.), 5 µl of 10×reaction buffer (0.5M Tris HCl, pH=8.5; 0.4M KCl; 0.1M MgCl$_2$; 4 mM DTT), 10 µl of a nucleotide solution (dGTP, dATP, dTTP, and dCTP, each at a concentration of 5 mM), 5 µl random primer, 0.25 µl of $^{32}$P-dCTP, 2 µl AMV reverse transcriptase, and 2 µl of RNASIN (Promega), in a total reaction volume of 50 µl. This mixture was incubated for one hour at 42° C.

(ii) Second Strand cDNA Synthesis

To the first strand synthesis reaction mixture the following components were added: 55 µl of 2×second strand synthesis buffer (50 mM Tris HCl, pH=7.0; 60 mM KCl); 2 µl RNase H; 5 µl DNA polymerase I, and 2 µl of the above described nucleotide solution. The reaction was incubated for one hour at 12° C., followed by a one hour incubation at room temperature. The reaction mixture was extracted with an equal volume of 1:1 phenol/chloroform, followed by an extraction using 24:1 chloroform/isoamyl alcohol. To each reaction mixture 1 µl of 10 mg/ml tRNA was added as carrier. The cDNA was precipitated by the addition of two volumes of 100% ethanol and chilling at −70° C. for 15 minutes. The cDNA was collected by centrifugation, the pellet washed with 70% ethanol and dried under vacuum.

(iii) Preparation of the Double Stranded cDNA for cloning

To provide vector compatible ends each of the double stranded cDNA preparations was tailed with EcoRI linkers in the following manner.

The cDNA was treated with EcoRI methylase under the following conditions: The cDNA pellet was resuspended in 20 µl 1×methylase buffer (50 mM Tris HCl, pH=7.5; 1 mM EDTA; 5 mM DTT), 2 µl 0.1 mM S-adenosyl-methionine (SAM) and 2 µl EcoRI methylase (New England Biolabs). The reaction was incubated for 30 minutes at 37° C. TE buffer (10 mM Tris-HCl, pH=7.5; 1 mM EDTA, pH=8.0) was added to achieve a final volume of 80 µl. The reaction mixture was extracted with an equal volume of phenol/chloroform (1:1) and then with an equal volume of chloroform/isoamyl alcohol (24:1). The cDNA was precipitated with two volumes of ethanol.

To maximize the number of blunt ends for the addition of linkers (Maniatis et al, 1982) the cDNA was then treated with the Klenow fragment of DNA polymerase I. The pelleted cDNA was resuspended in 11.5 μl of distilled water. The following components were added to the resuspended cDNA: 4 μl of 5×NTB (10×NTB stock solution: 0.5M Tric.Cl pH=7.2; 0.1M MgSO4; 1 mM dithiothreitol (DTT); 500 μg/ml bovine serum albumin (BSA)); 3 μl 0.1M MgCl2, 1.5 μl 10GATC (a solution containing 10 mM of each nucleotide G, A, T, and C), and 1 μl Klenow (Boehringer Mannheim Biochemicals). The reaction mixture was incubated at room temperature for 30 minutes. The reaction mixture was extracted with phenol/chloroform and chloroform isoamyl alcohol as described above, and then precipitated with two volumes of ethanol.

The cDNA pellet was resuspended in 12 μl distilled water. To the resuspended linkers the following components were added: 5 μl EcoRI phosphorylated linkers (New England Biolabs), 2 μl 10×ligation buffer (0.66M Tris.Cl pH=7.6, 50 mM MgCl2, 50 mM DTT, 10 mM ATP) and 1 μl T4 DNA ligase. The reaction was incubated at 14° C. overnight. The following morning the reaction was incubated at 67° C. for three minutes to inactivate the ligase, then momentarily chilled. To the ligation reaction mixture 2.5 μl of 10×high salt restriction digest buffer (Maniatis et al.) and 2.5 μl of EcoRI enzyme were added and the mixture incubated at 37° C. for at least 6 hours to overnight. To remove excess linkers the digestion mixture was loaded onto a 1.2% agarose gel and the reaction components size fractionated by electrophoresis. Size fractions of the 0.3–1.3 Kb and 1.3–7 Kb ranges were electroeluted onto NA45 paper (Schleicher and Schuell). The NA45 paper, with the eluted cDNA bound to it, was placed in a 1.5 ml microfuge tube containing 0.5 ml of elution solution (50 mM arginine, 1M NaCl, pH=9.0). The tube was then placed at 67° C. for approximately one hour to allow the cDNA to be eluted from the paper into the solution. The solution was then phenol/chloroform, chloroform/isoamyl alcohol extracted and precipitated with two volumes of ethanol. The resulting cDNA pellets were resuspended in 20 μl TE (pH=7.5).

(iv) Cloning of the cDNA into Lambda Vectors

The linkers used in the construction of the cDNAs contained an EcoRI site which allowed for direct insertion of the amplified cDNAs into lambda gt10 and gt11 vectors (Promega, Madison Wis.). Lambda vectors were purchased from the manufacturer (Promega) which were already digested with EcoRI and treated with bacterial alkaline phosphatase, to remove the 5' phosphate and prevent self-ligation of the vector.

The EcoRI-linkered cDNA preparations were ligated into both lambda gt10 and gt11 (Promega). The conditions of the ligation reactions were as follows: 1 μl vector DNA (Promega, 0.5 mg/ml); 0.5 or 3 μl of insert cDNA; 0.5 μl 10×ligation buffer (0.5M Tris-HCl, pH=7.8; 0.1M MgCl2; 0.2M DTT; 10 mM ATP; 0.5 g/ml BSA), 0.5 μl T4 DNA ligase (New England Biolabs) and distilled water to a final reaction volume of 5 μl.

The ligation reaction tubes were placed at 14° C. overnight (12–18 hours). The ligated cDNA was packaged the following morning by standard procedures using a lambda DNA packaging system (GIGAPAK, Stratagene, LaJolla, Calif.), and then plated at various dilutions to determine the titer and recombinant frequency of the libraries. A standard X-gal blue/white assay was used to screen the lambda gt11 libraries (Miller; Maniatis et al.). E. coli HG415 (from Howard Gersenfeld, Dept. of Pathology, Stanford School of Medicine) plating bacteria, which allows only plaque formation by recombinant clones, was used for plating the lambda gt10 libraries. The standard strain, E. coli C600hF−, may be used as an alternative to E. coli HG415.

Example 2

Screening the cDNA library for production of PT-NANBH antigens

The five lambda gt11 libraries generated in Example 1 were screened for specific HCV encoded viral antigens by immuno-screening. The phage were plated for plaque formation using the Escherichia coli bacterial plating strain E. coli KM392 (Kevin Moore, DNax, Palo Alto, Calif.). Alternatively, E. coli Y1088 may be used. The fusion proteins expressed by the lambda gt11 clones were screened with serum antibodies (Young et al.) from the following sources: chimpanzee #771 and various human PT-NANBH sera (including EGM, BV, WEH and AG).

From the lambda gt11 libraries (Example 1) approximately 111 independent clones gave a positive immunological reaction with at least one of the chimp or human PT-NANBH sera. These phage clones were plaque purified and the recombinant phage grown for DNA purification (Maniatis et al.).

Example 3

Genomic Hybridization Screening of Immunopositive Clones

Out of the 111 plaque purified recombinant phage, obtained as in Example 2, 93 were isolated (Maniatis et al.) and digested with EcoRI as per the manufacturer's instructions (Bethesda Research Laboratories, Gaithersburg, Md.). Approximately 1.0 microgram of each digested phage DNA sample was loaded into sample wells of 1.0% agarose gels prepared using TAE (0.04 m Tris Acetate, 0.001M EDTA). The DNA samples were then electrophoretically separated. DNA bands were visualized by ethidium bromide staining (Maniatis et al.). Inserts were clearly identified for each of the 93 clones, purified by electroelution using NA45, and then radioactively labelled by nick translation (Maniatis et al.).

Human peripheral blood lymphocyte (PBL) DNA was restriction digested with HindIII and EcoRI, loaded on a 0.7% agarose gel (as above, except 10 μg of DNA was loaded per lane) and the fragments separated electrophoretically. The DNA fragments in the agarose gels were transferred to nitrocellulose filters (Southern) and the genomic DNA probed with the nick-translated lambda gt11 inserts which were prepared above.

The filters were washed (Southern; Maniatis et al.) and exposed to X-ray film. Forty-three of the 93 lambda clone inserts displayed a positive hybridization reaction with the human PBL DNA. Among the remaining inserts which clearly did not hybridize with the PBL DNA, were 11 inserts derived from chimp #771 clones which were also clearly immunopositive from Example 2. Of these 11 clones, two of the clones had the immunoreactive characteristics summarized in Table 1. Chinmpanzee #771 and humans Ag, BV and WEH were chronimc PT-NANBH sera samples and SKF was a normal human serum sample.

TABLE 1

| Sera | Clone Designation | |
|---|---|---|
| | 36 | 40 |
| #771 | + | + |
| AG | + | − |
| BV | + | − |
| WEH | − | − |
| SKF | − | − |

Clone 40 (original clone screening designation 304-12-1) was clearly exogenous, i.e., not derived from normal human DNA, as evidenced by repeated hybridization tests against normal human PBL DNA, and a second clone, designated clone 36, (original clone screening designation 303-1-4) was not only exogenous but also reactive with multiple PT-NANBH antisera.

Example 4

Sequencing of Clones

DNA sequencing was performed on clones 36 and 40 as described in Example 3. Commercially available sequencing primers (New England Biolabs) homologous to flanking lambda sequences at the 5′ and 3′ ends of the inserts were initially used for sequencing. As sequencing progressed primers were constructed to correspond to newly discovered sequences. Synthetic oligonucleotide primers were prepared using commercially available automated oligonucleotide synthesizers. Alternatively, custom designed synthetic oligonucleotides may be purchased, for example, from Synthetic Genetics (San Diego, Calif.).

DNA sequences were determined for the complete insert of clone 40 (presented as SEQ ID NO:1 and also shown in FIG. 3); this sequence corresponds to nucleotides 6516 to 7070 of the HCV genome (FIGS. 8(A) to 8(H)). Subsequently, the inserts present in clones 44 and 45 (2 other clones of the 11 clones identified in Example 3) were found to cross-hybridize to the clone 40 insert. Partial sequencing of clones 44 and 45 showed that the sequences obtained from these two clones matched the sequence of clone 40. A partial sequence of the clone 36 insert was determined and is presented as SEQ ID NO: 3: the complete sequence is presented as SEQ ID NO:5 and is also shown in FIG. 4. The sequence of clone 36 corresponds to nucleotides 5010 to 6515 given in the FIGS. 8(A) to 8(H).

Example 5

Screening of the cDNA library in lambda gt10

The cDNA libraries in lambda gt10, generated in Example 1, were screened for the presence of sequences homologous to the clone 40 insert.

The lambda gt10 libraries were plated at a density of approximately $10^4$ plaques/plate and plaques lifts were prepared according to Maniatis et al. Filters were indexed using india ink to allow alignment of the filters with the parent plate from which the plaque lift was performed. The bacteria and phage particles were lysed, and the nitrocellulose filters were processed and baked as previously described (Maniatis et al.). The prehybridization solution, per filter, consisted of the following: 5.4 ml prehybridization buffer (50 ml of 1M Tris HCl, pH=7.5; 2 ml of 0.5M EDTA, pH=8.0; 50 ml of 10% SDS; 150 ml of 20×SSC (Maniatis et al.); and, 238 ml of glass distilled water); 6.0 ml formamide; 0.4 ml 50×Denhardt solution (5 g FICOLL; 5 g polyvinylpyrrolidone; 5 g bovine serum albumin; brought to a total volume of 500 ml with glass distilled water); and 0.2 ml of single-stranded salmon sperm DNA (10 mg/ml). Each filter was placed in a plastic bag and the prehybridization solution was added. The bag was sealed and incubated at 37° C. overnight with intermittent mixing of contents.

The clone 40 lambda DNA was isolated (Maniatis et al.) and digested with EcoRI. The resulting fragments were fractionated on an agarose gel and visualized by ethidium bromide staining (Maniatis et al.). The DNA fragment corresponding to the clone 40 insert, approximately 500 base pairs, was isolated from the agarose by electroelution onto NA45. The aqueous suspension of the purified fragment was extracted once with a 1:1 phenol/chloroform solution, and once with a 24:1 chloroform/isoamylalcohol solution. The DNA was then precipitated with ethanol and resuspended in sterile water.

The clone 40 insert was radioactively labelled by nick translation and used to probe the lambda gt10 plaque lift filters. The prehybridization solution was removed from the filters. Each filter was hybridized with probe under the following conditions: 5.0 ml of hybridization buffer (5 ml of 1M Tris HCl, pH=7.5; 0.2 ml of 0.5M EDTA, pH=8.0; 5.0 ml of 10% SDS; 14.9 ml of 20×SSC (Maniatis et al.); 10 g of dextran sulfate; and, glass distilled water to a total volume of 50 ml); 5.0 ml formamide; 0.4 ml 50×Denhardt's solution (5 g FICOLL; 5 g polyvinylpyrrolidone; 5 g bovine serum albumin; brought to a total volume of 500 ml with glass distilled water); and 0.2 ml of single-stranded salmon sperm DNA (10 mg/ml). To this hybridization mix was added 50–250 μl of denatured probe (boiled 5–10 minutes and quick-chilled on ice), resulting in approximately $10^6$ cpm of labelled probe per filter. The hybridization mix containing the labelled probe was then added to the plastic bag containing the filters. The bag was resealed and placed under a glass plate in a 37° C. water bath overnight with intermittent mixing of contents.

The next day the hybridization solution was removed and the filters washed three times, for 5 minutes each, in 2×SSC (Maniatis et al.) containing 0.5% SDS, at room temperature. The filters were then washed for one hour in 2×SSC, containing 0.5% SDS, at 50° C. The filters were then washed for 15–60 minutes in 0.1×SSC, containing 0.1% SDS, at 50° C. and finally 2×SSC, 15 minutes, 2–3× at room temperature. The washed filters were dried and then exposed to X-ray film for detection of positive plaques.

Approximately 24 plaques from the lambda gt10 libraries were plaque purified from the approximately 200 plaques which tested positive by the hybridization screen (Table 2).

TABLE 2

| Library | cDNA Source | Positives/ Plate |
|---|---|---|
| EGM | Human | ≈50 |
| BV | Human | ≈100 |
| WEH | Human | ≈25 |
| #771 | Chimp | ≈10–15 |

Example 6

Analysis of lambda gt10 cDNA Library Clones Homologous to the Clone 40 insert The clones identified in Example 5 which have homology to the clone 40 insert were analyzed by standard restriction analysis and the insert sizes were determined. The original frequencies of positive hybridization signals per plate using the clone 40 insert as probe against the different cDNA sources are shown in the last column of Table 2. That these positive signals arose with different frequencies for the different cDNA sources in the lambda gt10 library suggests that the hybridization signals originated from the sera source rather than common contamination introduced during cDNA synthesis or cloning.

One of the clones (108-2-5) from the EGM-generated cDNA library identified by hybridization with the clone 40 insert, had an insert of approximately 3.7 kb and was chosen for further analysis. The insert was isolated by EcoRI digestion of the clone, electrophoretic fractionation, and electroelution (Example 5). The insert was treated with DNase I under conditions resulting in partial digestion (Maniatis et al.) to generate random fragments. The resulting fragments were inserted into lambda gt11 vectors for expression. The lambda gt11 clones were then immunoscreened (Example 2) using human (BV and normal) and chimpanzee #771 sera. Twelve positive clones were identified by first round immunoscreening with the human and chimp sera. Seven of the 12 clones were plaque purified and rescreened using chimp serum (#771). Partial DNA sequences of the insert DNA were determined for two of the resulting clones that had the largest sequences, designated 328-16-1 and 328-16-2. The 2 clones had sequences essentially identical to clone 40.

Example 7

Preparing Amplified HCV cDNA Fragments

A. Preparing cDNA fragments

A plasma pool obtained from a chimpanzee with chronic PT-NANBH was obtained from the Centers for Disease Control (CDC) (Atlanta, Ga.). After direct pelleting or PEG precipitation, RNA was extracted from the virions by guanidinium thiocyanate-phenol-chloroform extraction, according to published methods (Chomczynski). The pelleted RNA was used for cDNA synthesis using oligo dT or random primers, or HCV sequence-specific primers and a commercial cDNA kit (Boehringer-Mannheim).

In one method, synthesis of first strand cDNA was achieved by addition of four primers, designated A, B, C, and D, having the sequences shown below. These sequences are complementary to the HCV genomic regions indicated:

A: 5'-GCGGAAGCAATCAGTGGGGC-3', complementary to basepairs 394-413;

B: 5'-GCCGGTCATGAGGGCATCGG-3', complementary to basepairs 2960-2980;

C: 5'-CGAGGAGCTGGCCACAGAGG-3', complementary to basepairs 5239-5258; and

D: 5'-TGGTTCTATGGAGTAGCAGGCCCCG-3', complementary to basepairs 7256-7280.

Second strand cDNA synthesis was performed by the method of Gubler and Hoffman. The reactions were carried out under standard cDNA synthesis methods given in the commercial kit.

B. Amplifying the cDNA Fragments

The cDNA from above was blunt ended and ligated to the linker/primer having the following sequence:

Linker/primer:

5'-GGA ATT CGC GGC CGC TCG-3'   A-strand
    3'-TT CCT AAG GCG CCG GCG AGC-5' B-strand The cDNA and linker were mixed at a 1:100 molar ratio in the presence of 0.3 to 0.6 Weiss units of T4 DNA ligase. To 100 $\mu$l of 10 mM Tris-Cl buffer, pH 8.3, containing 1.5 mM $MgCl_2$ and 50 mM KCl (Buffer A) was added about $1 \times 10-3$ $\mu$g of the linker-ended cDNA, 2 $\mu$M of linker/primer A (A-strand) having the sequence d(5'-GGAATTCGCGGCCGCTCG-3'), 200 $\mu$M each of dATP, dCTP, dGTP, and dTTP, and 2.5 units of *Thermus aquaticus* DNA polymerase (Taq polymerase). The reaction mixture was heated to 94° C. for 30 sec for denaturation, allowed to cool to 50° C. for 30 sec for primer annealing, and then heated to 72° C. for 0.5-3 minutes to allow for primer extension by Taq polymerase. The replication reaction, involved successive heating, cooling, and polymerase reaction, was repeated an additional 25 times with the aid of a Perkin-Elmer Cetus DNA thermal cycler. This results in a pool of SISPA (sequence-independent single primer amplification)-amplified DNA fragments.

Example 8

Preparing primer-Pair Fragments

Amplified cDNA fragments from Example 7 were mixed with 100 $\mu$l Buffer A, 1 $\mu$M of equal molar amounts of one of the primer pairs given below, 200 $\mu$M each of dATP, dCTP, dGTP, and dTTP, and 2.5 units of *Thermus aquaticus* DNA polymerase (Taq polymerase). Each primer pair includes a forward (upstream) primer $F_i$ which is identical to the coding strand at the upstream end of an overlap region $P_i$ of duplex genomic DNA, and a reverse primer $R_i$ which is complementary to the coding at the downstream end of the region $P_i$. The sets of primers each define an overlap region of about 200 basepairs, and the spacing between adjacent overlapping primer regions (i.e., between adjacent pairs of $F_i/R_i$ pairs) is about 0.5-1 kilobase. The regions of HCV which are complementary to the primers are given below:

$F_1$, basepairs 183-201; $R_1$, basepairs 361-380
$F_{10}$, basepairs 576-595; $R_{10}$, basepairs 841-860
$F_2$, basepairs 1080-1100; $R_2$, basepairs 1254-1273
$F_3$, basepairs 1929-1948; $R_3$, basepairs 2067-2086
$F_4$, basepairs 2754-2733; $R_4$, basepairs 2920-2940
$F_5$, basepairs 3601-3620; $R_5$, basepairs 3745-3764
$F_6$, basepairs 4301-4320; $R_6$, basepairs 4423-4442
$F_{12}$, basepairs 4847-4865; $R_{12}$, basepairs 4715-4734
$F_7$, basepairs 5047-5066; $R_7$, basepairs 5200-5216
$F_8$, basepairs 5885-5904; $R_8$, basepairs 6028-6047
$F_9$, basepairs 6902-6921; $R_9$, basepairs 7051-7070

Polymerase Chain Reaction (PCR) amplification of the SISPA-amplified cDNA fragments with each $F_i/R_i$ primer pair was carried out under conditions similar to those used above, with about 25 cycles.

The amplified fragment mixtures from above were each fractionated by electrophoresis on 1.5% agarose and transferred to nitrocellulose filters (Southern). Hybridization of the nitrocellulose-bound fragments, each with an internal-sequence oligonucleotide probe confirmed that each fragment contained the expected sequences. Hybridization was carried out with an internal oligonucleotide radiolabeled by polynucleotide kinase, according to standard methods.

Example 9

Preparing Linking Fragments

This example describes preparing large overlapping linking fragments of the HCV sequence. SISPA-amplified cDNA fragments from Example 7 were mixed with 100 μl Buffer A, 1 μM of equal molar amounts of forward and reverse primers in each of the primer pairs given below, 200 μM each of dATP, dCTP, dGTP, and dTTP, and 2.5 units of *Thermus aquaticus* DNA polymerase (Taq polymerase), as in Example 8. Each primer pair includes a forward primer $F_i$ and a reverse primer $R_j$, where $F_i$ is the forward primer for one overlap region $P_i$, and $R_j$ is the reverse primer of the adjacent overlap region. Thus each linking fragment spans two adjacent overlap regions. The sets of primers each define a linking fragment of about 0.5–1 kilobases. The sequences of the primer pairs are given in Example 8. The overlapping linking fragments of the HCV sequence (FIGS. 8(A) to 8(H)) spanned by each primer pair is given below:

$F_1/R_{10}$, basepairs 183–860
$F_{10}/R_2$, basepairs 576–1273
$F_2/R_3$, basepairs 1080–2086
$F_3/R_4$, basepairs 1929–2940
$F_4/R_5$, basepairs 2754–3762
$F_5/R_6$, basepairs 3601–4442
$F_6/R_{12}$, basepairs 4301–4865
$F_{12}/R_7$, basepairs 4715–5216
$F_7/R_8$, basepairs 5047–6047
$F_8/R_9$, basepairs 5885–7070

Two-primer amplification of the SISPA-amplified cDNA fragments with each $F_i/R_j$ primer pair was carried out under conditions similar to those described above, with about 25 cycles.

The amplified fragment mixtures from above were each fractionated by agarose electrophoresis on 1.2% agarose, and transferred to nitrocellulose filters (Southern) for hybridization with radiolabeled internal oligonucleotide probes as above. The analysis confirmed that each linking fragment contained the two end-primer sequences from adjacent overlap regions. The sequences contained in each of the linking fragments are indicated in FIGS. 8(A) to 8(H).

Example 10

Preparing Cloned Peptide Fragments

A. DNA Fragment Digestion

Each of the ten linking fragments from Example 9 was suspended in a standard digest buffer (0.5M Tris HCl, pH 7.5; 1 mg/ml BSA; 10 mM MnCl2) to a concentration of about 1 mg/ml and digested with DNAse I at room temperature for various times (1–5 minutes). These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers. The resultant fragments were analyzed by electrophoresis (5–10 V/cm) on 1.2% agarose gels, using PhiX174/HaeIII and lambda/HindIII size markers. The 100–300 bp fraction was eluted onto NA45 strips (Schleicher and Schuell), which were then placed into 1.5 ml microtubes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 μl TE buffer (0.01M Tris HCl, pH 7.5, 0.001M EDTA).

B. Cloning the Digest Fragments

Lambda gt11 phage vector (Young et al.) was obtained from Promega Biotec (Madison, Wis.). This cloning vector has a unique EcoRI cloning site 53 base pairs upstream from the beta-galactosidase translation termination codon. The partial digest fragments from each linking fragment in Part A were introduced into the EcoRI site by mixing 0.5–1.0 μg EcoRI-cleaved lambda gt11, 0.3–3 μl of the above sized fragments, 0.5 μl 10×ligation buffer (above), 0.5 μl DNA ligase (200 units), and distilled water to 5 μl. The mixture was incubated overnight at 14° C., followed by in vitro packaging, according to standard methods (Maniatis, pp. 256–268).

The packaged phage were used to infect *E. coli* strain KM392, obtained from Dr. Kevin Moore, DNAX (Palo Alto, Calif.). Alternatively, *E. coli* strain Y1090, available from the American Type Culture Collection (ATCC No. 37197), could be used. A lawn of KM392 cells infected with about $10^3$–$10^4$ pfu of the phage stock from above was prepared on a 150 mm plate and incubated, inverted, for 5–16 hours at 37° C. The infected bacteria were checked for loss of beta-galactosidase activity (clear plaques) in the presence of X-gal using a standard X-gal substrate plaque assay method (Maniatis).

Identification of single plaques containing a digest-fragment insert was confirmed as follows. Clear single plaques (containing the progeny of a single phage) were removed from the plate and suspended in extraction buffer (Maniatis) to release the phage DNA. The phage extract was added to the above DNA amplification mixture in the presence of primers which are about 70 basepairs away in either direction from the EcoRI site of lambda gt11. Thus phage containing a digest-fragment insert will yield an amplified digest fragment of about 140 basepairs plus insert. Phage DNA amplification was carried out as described above, with 25 cycles of amplification. The reaction material from each plaque tested was fractionated on 1.5% agarose, and examined for the size of amplified digest fragments. Non-recombinant phage gave a 140 basepair band, and recombinant phage, a band which is 140 basepair plus the insert sequence in size. The results are shown in column 2 (REC Freq) of Table 3 below, for the six linking-fragment libraries indicated in the first column in Table 3 below. The denominator in the column-2 entries is the total number of plaques assayed by primer amplification. The numerator is the number of clear plaques containing fragment inserts. Thus, 3/15 means that 3 plaques tested positive by PCR out of a total of 15 clear plaques assayed.

TABLE 3

| Library[1] | REC Freq[2] | 1° Screen[3] | PA/REC[4] |
| --- | --- | --- | --- |
| F2R3 #2 | 3/15 | 2 | 0.33 |
| F3R4 #1 | 7/12 | 0 | — |
| F4R5 #3 | 9/10 | 10 | 0.37 |
| F5R6 #5 | 11/12 | 37 | 1.35 |
| F7R8 #7 | 0/12 | 1 | — |
| F8R9 #10 | 3/12 | 58 | 7.73 |

[1] Libraries constructed by partial DNaseI Digestion of indicated linking clone
[2] Recombinant frequency determined by PCR with insert flanking lambda gt11 primers
[3] Primary screening with chronic human PT—NANBH serum (1:100) on 1.5 × phage
[4] PA/REC indicates the number of positive areas detected per actual number of recombinant plated The library of digest fragments constructed for each linking fragment was screened for expression of peptides which are immunoreactive with a human PT-NANBH serum. The lawn of phage-infected bacteria was overlaid with a nitrocellulose sheet, transferring PT-NANBH recombinant peptides from the plaques to filter paper. The plate and filter were indexed for matching corresponding plate and filter positions.

The filter was removed after 6–12 hours, washed three times in TBS buffer (10 mM Tris, pH 8.0, 150 mM NaCl), blocked with AIB (TBS buffer with 1% gelatin), washed again in TBS, and incubated overnight with of antiserum (diluted to 1:100 in AIB, 12–15 ml/plate). The sheet was washed twice in TBS and then incubated with alkaline-phosphatase-conjugated anti-human IgG to attach the labeled antibody at filter sites containing antigen recognized by the antiserum. After a final washing, the filter was developed in a substrate medium containing 33 μl NBT (50 mg/ml stock solution maintained at 4° C.) mixed with 16 μl BCIP (50 mg/ml stock solution maintained at 4 ° C.) in 5 ml of alkaline phosphatase buffer (100 mM Tris, 9.5, 100 mM NaCl, 5 mM MgC12). Reacted substrate precipitated at points of antigen production, as recognized by the antiserum.

The total number of plaques which showed antigen-positive reaction (positive areas PA) in the primary screen are given in the third column in Table 3. The fourth column in the table is the frequency of positive areas per total number of recombinant phage screened ($\times 10^3$). This last column is therefore a measure of the relative immunogenicity of antigen expressed from a particular linking fragment using this particular serum sample.

Example 11

Screening Digest Fragments

The digest-fragment libraries of each of the ten linking fragments from Example 9 were screened with sera from a human patient with chronic PT-NANBH and with pooled sera from chimpanzees with acute PT-NANBH infection and chronic PT-NANBH infection. Individual chronic and acute chimpanzee sera from 5 chimpanzees were obtained from the Centers for Disease Control.

The digest-fragment libraries from the linking fragments indicated in Table 4 below were screened with each of the three sera, using the screening procedure described in Example 10. The total number of positive areas observed in each plate (making up one fragment library) is given in the table. The entries in the table which are not in parentheses represent the number of positive areas which were confirmed by plaque purification, i.e., by replating plaques from the positive areas at low dilution and confirming a positive area (secondary screen). Typically about 90–95 percent of the positive areas in the primary screen tested positive by secondary screening. The entries in parentheses indicate positive areas which have not been confirmed in a secondary screen.

As seen from Table 4, all but one of the linking fragment libraries contained sequences encoding peptide antigens which are immunoreactive with either chronic human or chimpanzee infected sera. Five of the libraries contain sequences encoding antigens which are immunoreactive with acute sera, indicating that one or more of the antigens in this group are effective to detect acute-infection serum. Three of these latter libraries—$F_3/R_4$, $F_{12}/R_7$, and $F_7/R_8$—gave over 10 positives in each library. These data are not corrected for the recombinant frequency in a particular library and therefore do not reflect the comparative immunogenicity of the various linking fragments.

TABLE 4

| | Human P.P. Clones | Acute Pool P.P. Clones | Chronic Pool P.P. Clones |
| --- | --- | --- | --- |
| F1R10 | 0 | 0 | 0 |
| F10R2 | 4 | 2 | 4 |
| F2R3 | 4 | 0 | 1 |
| F3R4 | 0 | 10 | 10 |
| F4R5 | 5 | 0 | 7 |
| F5R6 | 34 | 0 | (42) |
| F6R12 | (400) | 5 | 10(200) |
| F12R7 | 2 | 17(200) | 9(200) |
| F7R8 | 0 | 20 | 10(130) |
| F8R9 | 60 | 0 | 1 |

( ) = not plaque purified
P.P. = Plaque Pure
Acute Pool = CDC Panel of Chimps
Chronic Pool = CDC Panel of Chimps

Example 12

Immunoscreening for 409-1-1-Antigen

A. Plaque Immunoscreening

Several clear plaques identified in the primary screen of the $F_4/R_5$ linking fragment were replated and plaque purified. One of the purified plaques was designated gt11/409-1-1(c-a). The digest fragment contained in clone 409-1-1(c-a) corresponds to two sets of base pairs present in the HCV genome and present in clone 409-1-1(abc). For ease of reference three regions (a, b, and c,) have been designated in the 409-1-1(abc) clone (see below and FIG. 5). The longest homology of base pairs corresponds approximately to nucleotides 2754 to 3129 of FIGS. 8(A) to 8(H) (the "a" region, see FIG. 5, region delineated by boxes) and the shorter homology corresponds approximately to nucleotides 3242 to 3311 of FIGS. 8(A) to 8(H) (the "c" region, see FIG. 5): normally the "c" region is located approximately 112 nucleotides distal the 3' end of the "a" region (see FIG. 5). The complete sequence of the gt11/409-1-1(c-a) insert is given in FIGS. 6A and 6B and presented as SEQ ID NO:7. This clone arose through a ligation event between two independent DNaseI fragments generated from the $F_4/R_5$ linking clone and has ATCC No. 40792. A related clone, designated 409-1-1(abc), has been described in coowned patent application Ser. No. 505,611 and has ATCC No. 40876.

A lambda gt11 clone corresponding to the immunoreactive sequence reported in the EPO application 88310922.5, and designated 5-1-1, was prepared by primer-specific amplification of the amplified cDNA fragments generated in Example 7. The 5-1-1 sequence corresponds to basepairs 3730-3858 of the HCV sequence FIGS. 8(A) to 8(H)), in the linking fragment F5/R6. The primers used for fragment amplification are 20 basepair oligomers complementary to the forward and reverse sequences of the 3732-3857 basepair 5-1-1 sequence. Both oligomers have EcoRI sites incorporated into their ends and the forward oligomer is designed to ensure a contiguous open reading fram with the beta-galactosidase gene. The amplified 5-1-1 sequence was purified by agarose gel electrophoresis, and cloned into lambda gt11 phage. Amplification and cloning methods were as described above. Phage containing the 5-1-1 sequence were identified and purified by primary and secondary screening, respectively, with human PT-NANBH serum, also as described above.

The purified gt11/409-1-1(c-a) and gt11/5-1-1 clones were each mixed with negative lambda gt11 phage, plated and immunoscreened with a number of different donor sera from normal and NANBH-infected humans and chimpanzees, as indicated in Table 5 below. Each plate was divided into several equal-area sections, and the corresponding sections on the nitrocellulose transfer filter were separately screened with the donor sera indicated, using the immunoscreening method described in Example 11. The number of positives detected for each group of sera by the 5-1-1 and 409-1-1 (c-a) peptides are shown, as well as a comparison with the C-100 test in the ELI SA format, in Table 5.

TABLE 5

| Source | Diagnosis | # Donors | # Positive 5-1-1 | 409-1-1 (c-a) | C-100 |
|--------|-----------|----------|-------|---------------|-------|
| Human | Normal | 2 | 0 | 0 | NT |
| Human | NANB | 6 | 4 | 5 | 0/1* |
| Chimp | Normal | 7 | 0 | 0 | 0/5 |
| Chimp | Acute | 5 | 1 | 3 | 0/5 |
| Chimp | Chronic | 8 | 7 | 7 | 5/5 |

NT, not tested; *only BV serum was tested; N/5 means N positives out of five sera tested.

B. Western Blot Screening

For Western blot screening, gt11/409-1-1(c-a) phage from Example 11 was used to infect *E. coli* BNN103 temperature-sensitive bacteria. These bacteria were obtained from the American Type Culture Collection. The bacterial host allows expression of a beta-galactosidase/peptide antigen fused protein encoded by the vector under temperature induction conditions (Hunyh).

Infected bacteria were streaked, grown at 32° C. overnight or until colonies were apparent, and individual colonies were replica plated and examined for growth at 32° C. and 42° C. Bacterial colonies which grew at 32° C. but not 42° C., indicating integration of the phage genome, were used to inoculate 1 ml of NZYDT (Maniatis) broth A saturated overnight bacterial culture was used to inoculate a 10 ml culture, which was incubated with aeration to an O.D. of about 0.2 to 0.4, typically requiring 1 hour incubation. The culture was then brought to 43° C. quickly in a 43° C. water bath and shaken for 15 minutes to induce lambda gt11 peptide synthesis, and incubated further at 37° C. for 1 hour.

The cells were pelleted by centrifugation, and 1 ml of the pelleted material was resuspended in 100 μl of lysis buffer (62 mM Tris, pH 7.5 containing 5% mercaptoethanol, 2.4% SDS and 10% glycerol). Aliquots (about 15 μl) were loaded directly onto gels and fractionated by SDS-PAGE. After electrophoresis, the fractionated bands were transferred by electroelution to nitrocellulose filters, according to known methods (Ausubel et al.).

The lysate was treated with DNaseI to digest bacterial DNA, as evidenced by a gradual loss of viscosity in the lysate. An aliquot of the material was diluted with Triton X-100 TM and sodium dodecyl sulfate (SDS) to a final concentration of 2% Triton X-100 TM and 0.5% SDS. Non-solubilized material was removed by centrifugation and the supernatant was fractionated by SDS polyacrylamide electrophoresis (SDS-PAGE).PAGE, A portion of the gel was stained, to identify the peptide antigen of interest, and the corresponding unstained band was transferred onto a nitrocellulose filter.

The 5-1-1 antigen coding sequence (Example 11) was also expressed as a glutathione-S-transferase fusion protein using the pGEX vector system, according to published methods (Smith). The fusion protein obtained from bacterial lysate and fractionated by SDS-PAGE were transferred to a nitrocellulose filter for Western blotting, as above.

Western blotting was carried out substantially as described in Example 10. Briefly, the filters were blocked with AIB, then reacted with the serum samples identified in Table 5, including human and chimpanzee normal, chronic NANBH, and hepatitis B (HBV) sera sample. The presence of specific antibody binding to the nitrocellulose filters was assayed by further immunobinding of alkaline-phosphatase labelled anti-human IgG. The results of the Western blot analysis with the Sj26/5-1-1 fusion protein and/409-1-1(c-a) fusion proteins are shown in Table 6. The data confirm that 409-1-1(c-a) and 5-1-1 peptide antigens are specifically immunoreactive with human and chimpanzee NANBH antisera.

TABLE 6

| | | | # Positive | |
|--------|-----------|----------|-------------|---------------|
| Source | Diagnosis | # Donors | Sj26 5-1-1 | β-gal 409-1-1 (c-a) |
| Human | Normal | 2 | 0 | 0 |
| Human | NANB | 7 | 5 | 5 |
| Human | HBV | 1 | 0 | 0 |
| Chimp | Normal | 5 | 0 | 0 |
| Chimp | NANB | 6 | 5 | 5 |
| Chimp | HBV | 1 | 0 | 0 |

Example 13

Generation of Alternative Clones

Alternative clones were generated from the region identified in Example 12 as encoding antigen specifically immunoreactive with human and chimpanzee NANBH antisera. The primers shown in Table 7 were selected from the HCV or 409-1-1(abc) coding sequences to generate a variety of overlapping clones.

TABLE 7

| Primer | Sequence |
|--------|----------|
| 33C-F1 | CCGAATTCGCGGTGGACTTTATCCCTGT |
| 33C-R1 | CCGAATTCCAGAGCAACCTCCTCGATG |
| 409-1-1(c-a)F | CCGAATTCCGCACGCCCGCCGAGACTAC |
| 409-1-1-F1 | CCGAATTCTCCACCACCGGAGAGATCCC |
| 409-1-1-R2 | CCGAATTCCACACGTATTGCAGTCTATC |
| 409-1-1-F3 | CCGAATTCGTCACCCAGACAGTCGAT |
| 409-1-1-R5 | CCGAATTCCCCTCCCAAAATTCAAGATGG |
| 409-1-1(c-a) R | CCGAATTCGCCAGTCCTGCCCCGACGTT |

TABLE 7-continued

| Primer | Sequence |
|---|---|
| 409-1-1CR | CCGAATTCGTCCTGGCACACGGGAAG |

The primers shown in Table 7 were used in DNA amplification reactions as described in Examples 7B and 8: the primers and templates used in each reaction are shown in Table 8. The amplified fragments were then treated with the Klenow fragment of DNA polymerase I, under standard conditions (Maniatis et al.), to fill in the ends of the molecules. The blunt-end amplified fragments were digested with EcoRI under standard conditions and cloned into lambda gt11 expression vectors essentially as described in Example 10B. The resulting inserts are aligned for comparison in FIG. 7.

TABLE 8

| Generated Fragment | Template | Primers |
|---|---|---|
| 33C | cDNA* | 33-C-F1 and 409-1-1-R2 |
| 33CU | cDNA* | 33-C-F1 and 33-C-R1 |
| 409-1-1(F1R2) | gt11 409-1-1(c-a) | 409-1-1-F1 and 409-1-1-R2 |
| 409-1-1(a) | gt11 409-1-1(c-a) | 409-1-1-F1 and 409-1-1caR |
| 409-1-1(c) | gt11 409-1-1(c-a) | 409-1-1caF and 409-1-1CR |
| 409-1-1(c + 270) | gt11 409-1-1(c-a) | 409-1-1caF and 409-1-1-R2 |
| 409-1-1u | gt11 409-1-1(c-a) | 409-1-1-F3 and 409-1-1caR |

*Amplified cDNA fragments from Example 7

Example 13

Immunoscreening of the Alternative Clones

The alternative clones generated in Example 12 were immunoscreened essentially as described in Example 10B. Clones 409-1-1(abc) and 409-1-1(c-a), generated in Example 12, were also included in the following immunoscreenings. The results of the preliminary immunoscreening are shown in Table 9.

TABLE 9

|  | GLI-1 | FEC |
|---|---|---|
| 33C | + | ND* |
| 33cu | + | ND |
| 409-1-1 (abc) | + | ND |
| 409-1-1 (F1R2) | + | ND |
| 409-1-1 (a) | + | ND |
| 409-1-1 (ca) | + | ND |
| 409-1-1 (C) | − | − |
| 409-1-1 (c + 270) | + | ND |
| 409-1-1 u | − | − |

*Not Done

The GLI-1 sera was a human chronic PT-NANBH sera. If a clone tested negative with GLI-1 it was further examined by screening with FEC, a human chronic PT-NANBH sera.

The seven of the 9 alternative clones which tested positive by the above preliminary immunoscreening were more extensively screened against a battery of sera. In addition, clone C100 (see Background) was included in the screening. The results of this more exhaustive screening are presented in Table 10.

TABLE 10

| | ANTIGEN | | | | | | | |
|---|---|---|---|---|---|---|---|---|
| Serum | C100 | 33C | 33Cu | 409-1-1 abc | 409-1-1 F1R2 | 409-1-1 a | 409-1-1 c + 270 | 409-1-1 ca | 5-1-1 |
| SKF(−) | − | − | − | − | − | − | − | − | − |
| FEC(+) | + | +3 | +3 | +1 | +2 | +2 | − | +2 | +2 |
| BV | − | +2 | +3 | I | +1 | +1 | − | +1 | − |
| Bar | − | +2 | +2 | I | − | − | − | − | − |
| PP(−) | − | − | − | − | − | − | − | − | − |
| AP | − | +1 | +2 | − | I | − | − | I | − |
| CP | + | +2 | +3 | +2 | +3 | +3 | I | +3 | +2 |
| 1 | − | − | − | − | − | − | − | − | − |
| 2 | − | − | − | − | − | − | − | − | − |
| 3 | − | − | − | − | − | − | − | − | − |
| 4 | − | − | − | I | I | − | − | − | I |
| 5 | − | − | +1 | − | − | − | − | − | − |
| 6 | − | +1 | +3 | +1 | +1 | +1 | − | +1 | +1 |
| 7 | − | +2 | +3 | +1 | +2 | +2 | − | +2 | +1 |
| 38 | − | − | I | +1 | I | I | − | − | I |
| 39 | − | − | +1 | I | +1 | − | − | I | I |
| 40 | + | +1 | +2 | +1 | +1 | − | I | +1 | +1 |
| 41 | + | +2 | +3 | +1 | +1 | +1 | − | +2 | +1 |
| 42 | + | +2 | +2 | +1 | +1 | +1 | − | +2 | +1 |
| 43 | − | − | − | − | − | − | − | − | − |
| 44 | − | I | I | − | − | − | − | − | − |
| 45 | − | I | +1 | I | I | − | − | I | I |
| 46 | + | +1 | +2 | +1 | +2 | +1 | − | +1 | I |
| 47 | + | +1 | +2 | +2 | +2 | +3 | ≈ | +3 | +1 |
| B18 | − | +3 | +3 | +1 | +3 | +3 | − | +3 | − |
| A7 | − | +3 | +3 | +1 | +1 | +3 | − | +3 | +3 |
| C7 | − | +2 | +3 | − | − | − | − | − | − |
| A3 | − | +3 | +3 | +1 | +2 | +1 | − | +2 | − |
| B7 | − | +2 | +3 | I | +3 | +3 | − | +3 | I |
| C12 | + | +2 | +3 | − | − | − | − | − | − |

The serum samples used for screening were identified as follows: SKF, PT-NANBH negative; FEC, PT-NANBH positive; BV, community acquired NANBH; Bar, PT-NANBH positive; PP (pre-inoculation pooled chimpanzee serum), PT-NANBH negative; AP (acute HCV pooled chimpanzee serum), PT-NANBH positive; and, CP (chronic HCV pooled chimpanzee serum) PT-NANBH positive. The numbered serum samples correspond to human clinical serum samples which were PT-NANBH positive. The PP, CP, and AP sera were pooled sera samples from 5 different chimpanzees: the chimpanzee serum samples were obtained from the Centers for Disease Control. The scoring system presented in Table 10 is a qualitative scoring system defined as follows: (−), a clear negative; (+), (1+), (2+), (3+), increasing strength of positive signal, with (3+) being the strongest signal; and (I) stands for Indeterminate, where two readings were different and not repeated.

In view of the data presented in Table 10 the sensitivity of the antigens in terms of immunoscreening is 33cu>33c>409-1-1(c-a)>409-1-1-FIR2>409-1-1(abc)≧409-1-1a>5-1-1>409-1-1-(c+270). Although 33cu and 33c were sensitive antigens, they reacted with high background against all sera. Accordingly, the 409-1-1 series are more useful as diagnostic antigens since they are more specific to HCV induced antibodies.

The immunoscreening was further extended to include the clone 36 and 45 (corresponds to clone 40) encoded epitopes which were identified above. Table 11 shows the results of the immunoscreening.

TABLE 11

PANEL I: SEROCONVERSION SPECIMENS

| SERUM | ANTIGEN | | | | | |
|---|---|---|---|---|---|---|
| | C-100 | 33C | 5.1.1 | 409-1-1 (c-a) | 36 | 45 | gt11 |
| GLI-1 | + | 4+ | 2+ | 4+ | — | 3+ | — |
| FEC | + | 4+ | 3+ | 4+ | 3+ | — | — |
| BV | — | 3+ | — | 3+ | — | — | — |
| SKF(norm) | — | — | — | — | — | — | — |
| 1-N01/D69 | — | I | — | — | — | — | — |
| 2-N01/D124 | — | + | — | — | — | — | — |
| 3-N01/D146 | — | I | — | — | — | — | — |
| 4-N01/D211 | — | + | — | — | — | — | — |
| 5-N00/D22 | — | + | I | I | — | — | — |
| 6-N00/D29 | — | 2+ | + | 2+ | — | — | — |
| 7-N00/D41 | — | 3+ | 2+ | 3+ | — | — | — |
| 8-N00/D60 | — | 4+ | 3+ | 4+ | — | — | — |
| 9-N00/D137 | + | 4+ | 4+ | 4+ | 2+ | — | — |
| 10-N240/D0 | — | I | — | I | — | — | — |
| 11-N240/D45 | — | — | — | — | — | — | — |
| 12-N240/D71 | — | I | — | I | — | — | — |
| 13-N240/D89 | — | I | — | — | — | — | — |
| 14-N240/D106 | — | I | — | — | — | — | — |
| 15-N240/D155 | — | I | — | — | — | — | — |
| 16-N228/D0 | — | I | — | — | — | — | — |
| 17-N228/D31 | — | I | — | — | — | — | — |
| 18-N228/D41 | — | I | — | — | — | — | — |
| 19-N228/D51 | — | I | — | — | — | — | — |
| 20-N228/D73 | — | I | — | — | — | — | — |
| 21-N228/D93 | — | — | — | — | — | — | — |
| 22-N228/D127 | — | — | — | — | — | — | — |
| 23-N192/D114 | — | I | — | — | — | — | — |
| 24-N192/D184 | — | — | — | — | — | — | — |
| 25-N192/D224 | — | — | — | — | — | — | — |
| 26-N192/D280 | — | I | — | — | — | — | — |
| 27-N176/D0 | — | I | — | — | — | — | — |
| 28-N176/D66 | — | — | — | — | — | — | — |
| 29-N176/D77 | — | — | — | — | — | — | — |
| 30-N170/D94 | — | — | — | — | — | — | — |
| 31-N176/D200 | — | — | — | — | — | — | — |
| 32-N170/D0 | — | — | — | — | — | — | — |
| 33-N170/D27 | — | I | — | — | — | — | — |
| 34-N170/D49 | — | — | — | — | — | — | — |
| 35-N170/D64 | — | — | — | — | — | — | — |
| 36-N170/D183 | — | — | — | — | — | — | — |
| 37-N170/D278 | — | — | — | — | — | — | — |
| 38-N144/D63 | — | I | — | — | — | — | — |
| 39-N144/D72 | — | I | — | — | — | — | — |
| 40-N144/D91 | + | 2+ | + | 2+ | — | — | — |
| 41-N144/D289 | + | 4+ | + | 3+ | 2+ | — | — |
| 42-N144/D233 | + | 4+ | 3+ | 4+ | 2+ | — | — |
| 43-N122/D0 | — | I | — | — | — | — | — |
| 44-N122/D51 | — | I | I | I | — | — | — |
| 45-N122/D57 | — | 2+ | I | + | — | — | — |
| 46-N122/D72 | + | 2+ | — | 3+ | I | — | — |
| 47-N122/D94 | + | 3+ | + | 4+ | + | — | — |
| 48-N122/D199 | + | 4+ | 2+ | 4+ | + | — | — |
| 49-N31/D0 | — | I | — | — | — | — | — |
| 50-N31/D140 | — | — | — | — | — | — | — |
| 51-N31/D154 | — | — | — | — | — | — | — |

TABLE 11-continued

PANEL I: SEROCONVERSION SPECIMENS

| SERUM | ANTIGEN | | | | | |
|---|---|---|---|---|---|---|
| | C-100 | 33C | 5.1.1 | 409-1-1 (c-a) | 36 | 45 | gt11 |
| 52-N31/D170 | — | — | — | — | — | — | — |
| 53-N31/D210 | — | — | — | — | — | — | — |
| 54-N31/D266 | — | — | — | — | — | — | — |
| 55-N31/D336 | — | — | — | — | — | — | — |
| 56-N31/D394 | — | — | — | — | — | — | — |
| 57-N16/D0 | — | — | — | — | — | — | — |
| 58-N16/D47 | — | — | — | — | — | — | — |
| 59-N16/D62 | — | — | — | — | — | — | — |
| 60-N16/D83 | — | — | — | — | — | — | — |
| 61-N16/D137 | — | — | — | — | — | — | — |
| 61-N16/D167 | — | — | — | — | — | — | — |
| 63-N16/D197 | — | — | — | — | — | — | — |
| 64-N16/D370 | — | — | — | — | — | — | — |

The screening sera GLI-1, FEC, BV, and SKF have been defined above. The numbered sera samples correspond to human clinical serum samples which were PT-NANBH positive: these samples were obtained from Dr. Francoise Fabiani-Lunel, Hospital La Pitie salpetriere, Paris, France. As can be seen from the results presented in Table 11, the antigens produced by clones 36 and 40, while not as sensitive as 409-1-1(c-a), do yield HCV-specific immunopositive signals.

Example 14

Isolation of 409-1-1 Fusion Protein

Sepharose 4B beads conjugated with anti-beta galactosidase were purchased from Promega. The beads were packed in 2 ml column and washed successively with phosphate-buffered saline with 0.02% sodium azide and 10 ml TX buffer (10 mM Tris buffer, pH 7.4, 1% aprotinin).

BNN103 lysogens infected with gt11/409-1-1(c-a) from Example 12 were used to inoculate 500 ml of NZYDT broth. The culture was incubated at 32° C. with aeration to an O.D. of about 0.2 to 0.4, then brought to 43° C. quickly in a 43° C. water bath for 15 minutes to induce gt11 peptide synthesis, and incubated further at 37° C. for 1 hour. The cells were pelleted by centrifugation, suspended in 10 ml of lysis buffer (10 mM Tris, pH 7.4 containing 2% Triton X-100 TM and 1% aprotinin added just before use. The resuspended cells were frozen in liquid nitrogen, then thawed, resulting in substantially complete cell lysis. The lysate was treated with DNaseI to digest bacterial and phage DNA, as evidenced by a gradual loss of viscosity in the lysate. Non-solubilized material was removed by centrifugation.

The clarified lysate material was loaded on the Sepharose column, the ends of the column were closed, and the column was placed on a rotary shaker for 2 hrs. at room temperature and 16 hours at 4° C. After the column settled, it was washed with 10 ml of TX buffer. The fused protein was eluted with 0.1M carbonate/bicarbonate buffer, pH10. A total of 14 ml of the elution buffer was passed through the column, and the fusion protein eluted in the first 4–6 ml of eluate.

The first 6 ml of eluate from the affinity column were concentrated in Centricon TM -30 cartridges (Amicon, Danvers, Mass.). The final protein concentrate was resuspended in 400 μl PBS buffer. Protein purity was analyzed by SDS-PAGE. A single prominent band was observed.

Example 15

Preparation of Anti-409-1-1(c-a) Antibody

The 409-1-1(c-a) digest fragments from lambda gt11 were released by EcoRI digestion of the phage, and the "A" region purified by gel electrophoresis. The purified fragment was introduced into the pGEX expression vector (Smith). Expression of glutathione S-transferase fused protein (Sj26 fused protein) containing the 409-1-1(a) peptide antigen was achieved in *E. coli* strain KM392 (above). The fusion protein was isolated from lysed bacteria, and isolated by affinity chromatography on a column packed with glutathione-conjugated beads, according to published methods (Smith).

The purified Sj26/409-1-1(a) fused protein was injected subcutaneously in Freund's adjuvant in a rabbit. Approximately 1 mg of fused protein was injected at days 0 and 21, and rabbit serum was collected on days 42 and 56.

A purified Sj26/5-1-1 fused protein was similarly prepared using the an amplified HCV fragment encoding the 5-1-1 fragment. The fused Sj26/5-1-1 protein was used to immunize a second rabbit, following the same immunization schedule. A third rabbit was similarly immunized with purified Sj26 protein obtained from control bacterial lysate.

Minilysates from the following bacterial cultures were prepared as described in Example 12: (1) KM392 cells infected with pGEX, pGEX containing the 5-1-1 insert, and pGEX containing the 409-1-1(a) insert; and (2) BNN103 infected with lambda gt11 containing the 5-1-1 insert and gt11 containing the 409-1-1(c-a) insert. The minilysates were fractionated by SDS-PAGE, and the bands transferred to nitrocellulose filters for Western blotting as described in Example 12. Table 12 shows the pattern of immunoreaction which was observed when the five lysate preparations (containing the antigens shown at the left in the table) were screened with each of the three rabbit immune sera. Summarizing the results, serum from control (Sj26) rabbits was immunoreactive with each of the Sj26 and Sj26 fused protein antigens. Serum from the animal immunized with Sj26/5-1-1 fused protein was reactive with all three Sj-26 antigens and with the beta-gal/5-1-1 fusion protein, indicating the presence of specific immunoreaction with the 5-1-1 antigen. Serum from the animal immunized with Sj26/409-1-1(a) fused protein was reactive with all three Sj-26 antigens and with the beta-gal/409-1-1(c-a) fusion protein, indicating the presence of specific immunoreaction with the 409-1-1(a) antigen. None of the sera were immunoreactive with beta-galactosidase (obtained from a commercial source).

TABLE 12

| Antigens | Antibody | | |
|---|---|---|---|
| | Sj26 | 5-1-1/Sj26 | 409-1-1(a)/Sj26 |
| SJ26 | + | + | + |
| 5-1-1/ (Sj26) | + | + | + |
| 5-1-1/ (β-bal) | − | + | − |
| 409-1-1(a) (Sj26) | + | + | + |
| 409-1-1(c-a) (β-gal) | − | − | + |

Anti-409-1-1(a) antibody present in the sera from the animal immunized with the Sj26/409-1-1(a) is purified by affinity chromatography, following the general procedures described in Example 12, but where the ligand derivatized to the Sepharose beads is the purified beta-gal/409-1-1(c-a) fusion protein, rather than the anti-beta-galactosidase antibody.

Although the invention has been described with reference to particular embodiments, methods, construction and use, it will be apparent to those skilled in the art that various changes and modifications can be made without departing from the invention.

---

It is claimed:

1. A polypeptide composition for detecting the presence of antibodies immunoreactive with Hepatitis C Virus in a serum sample, comprising a polypeptide produced by bacterial cells containing lambda vector ATCC No. 40893, where said polypeptide contains the sequence presented as SEQ ID NO:2.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 561 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: N ( i v ) ANTI-SENSE: N ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: 304-12-1

( i x ) FEATURE:
        ( A ) NAME/KEY: CDS
        ( B ) LOCATION: 1..561
        ( D ) OTHER INFORMATION:

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GAA | TTC | CTC | GTG | CAA | GCG | TGG | AAG | TCC | AAG | AAA | ACC | CCA | ATG | GGG | TTC | 48 |
| Glu | Phe | Leu | Val | Gln | Ala | Trp | Lys | Ser | Lys | Lys | Thr | Pro | Met | Gly | Phe | |
| 1 | | | | 5 | | | | | 10 | | | | | 15 | | |
| TCG | TAT | GAT | ACC | CGC | TGC | TTT | GAC | TCC | ACA | GTC | ACT | GAG | AGC | GAC | ATC | 96 |
| Ser | Tyr | Asp | Thr | Arg | Cys | Phe | Asp | Ser | Thr | Val | Thr | Glu | Ser | Asp | Ile | |
| | | | 20 | | | | | 25 | | | | | 30 | | | |
| CGT | ACG | GAG | GAG | GCA | ATC | TAC | CAA | TGT | TGT | GAC | CTC | GAC | CCC | CAA | GCC | 144 |
| Arg | Thr | Glu | Glu | Ala | Ile | Tyr | Gln | Cys | Cys | Asp | Leu | Asp | Pro | Gln | Ala | |
| | | 35 | | | | | 40 | | | | | 45 | | | | |
| CGC | GTG | GCC | ATC | AAG | TCC | CTC | ACC | GAG | AGG | CTT | TAT | GTT | GGG | GGC | CCT | 192 |
| Arg | Val | Ala | Ile | Lys | Ser | Leu | Thr | Glu | Arg | Leu | Tyr | Val | Gly | Gly | Pro | |
| | 50 | | | | | 55 | | | | | 60 | | | | | |
| CTT | ACC | AAT | TCA | AGG | GGG | GAG | AAC | TGC | GGC | TAT | CGC | AGG | TGC | CGC | GCG | 240 |
| Leu | Thr | Asn | Ser | Arg | Gly | Glu | Asn | Cys | Gly | Tyr | Arg | Arg | Cys | Arg | Ala | |
| 65 | | | | | 70 | | | | | 75 | | | | | 80 | |
| AGC | GGC | GTA | CTG | ACA | ACT | AGC | TGT | GGT | AAC | ACC | CTC | ACT | TGC | TAC | ATC | 288 |
| Ser | Gly | Val | Leu | Thr | Thr | Ser | Cys | Gly | Asn | Thr | Leu | Thr | Cys | Tyr | Ile | |
| | | | | 85 | | | | | 90 | | | | | 95 | | |
| AAG | GCC | CGG | GCA | GCC | TGT | CGA | GCC | GCA | GGG | CTC | CAG | GAC | TGC | ACC | ATG | 336 |
| Lys | Ala | Arg | Ala | Ala | Cys | Arg | Ala | Ala | Gly | Leu | Gln | Asp | Cys | Thr | Met | |
| | | | 100 | | | | | 105 | | | | | 110 | | | |
| CTC | GTG | TGT | GGC | GAC | GAC | TTA | GTC | GTT | ATC | TGT | GAA | AGC | GCG | GGG | GTC | 384 |
| Leu | Val | Cys | Gly | Asp | Asp | Leu | Val | Val | Ile | Cys | Glu | Ser | Ala | Gly | Val | |
| | | 115 | | | | | 120 | | | | | 125 | | | | |
| CAG | GAG | GAC | GCG | GCG | AGC | CTG | AGA | GCC | TTC | ACG | GAG | GCT | ATG | ACC | AGG | 432 |
| Gln | Glu | Asp | Ala | Ala | Ser | Leu | Arg | Ala | Phe | Thr | Glu | Ala | Met | Thr | Arg | |
| | 130 | | | | | 135 | | | | | 140 | | | | | |
| TAC | TCC | GCC | CCC | CCC | GGG | GAC | CCC | CCA | CAA | CCA | GAA | TAC | GAC | TTG | GAG | 480 |
| Tyr | Ser | Ala | Pro | Pro | Gly | Asp | Pro | Pro | Gln | Pro | Glu | Tyr | Asp | Leu | Glu | |
| 145 | | | | | 150 | | | | | 155 | | | | | 160 | |
| CTC | ATA | ACA | TCA | TGC | TCC | TCC | AAC | GTG | TCA | GTC | GCC | CAC | GAC | GGC | GCT | 528 |
| Leu | Ile | Thr | Ser | Cys | Ser | Ser | Asn | Val | Ser | Val | Ala | His | Asp | Gly | Ala | |
| | | | | 165 | | | | | 170 | | | | | 175 | | |
| GGA | AAG | AGG | GTC | TAC | TAC | CTC | ACC | CGG | GAA | TTC | | | | | | 561 |
| Gly | Lys | Arg | Val | Tyr | Tyr | Leu | Thr | Arg | Glu | Phe | | | | | | |
| | | | 180 | | | | | 185 | | | | | | | | |

( 2 ) INFORMATION FOR SEQ ID NO:2:

( i ) SEQUENCE CHARACTERISTICS:
        ( A ) LENGTH: 187 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Glu | Phe | Leu | Val | Gln | Ala | Trp | Lys | Ser | Lys | Lys | Thr | Pro | Met | Gly | Phe |
| 1 | | | | 5 | | | | | 10 | | | | | 15 | |
| Ser | Tyr | Asp | Thr | Arg | Cys | Phe | Asp | Ser | Thr | Val | Thr | Glu | Ser | Asp | Ile |
| | | | 20 | | | | | 25 | | | | | 30 | | |
| Arg | Thr | Glu | Glu | Ala | Ile | Tyr | Gln | Cys | Cys | Asp | Leu | Asp | Pro | Gln | Ala |
| | | 35 | | | | | 40 | | | | | 45 | | | |
| Arg | Val | Ala | Ile | Lys | Ser | Leu | Thr | Glu | Arg | Leu | Tyr | Val | Gly | Gly | Pro |
| | 50 | | | | | 55 | | | | | 60 | | | | |
| Leu | Thr | Asn | Ser | Arg | Gly | Glu | Asn | Cys | Gly | Tyr | Arg | Arg | Cys | Arg | Ala |
| 65 | | | | | 70 | | | | | 75 | | | | | 80 |
| Ser | Gly | Val | Leu | Thr | Thr | Ser | Cys | Gly | Asn | Thr | Leu | Thr | Cys | Tyr | Ile |
| | | | | 85 | | | | | 90 | | | | | 95 | |
| Lys | Ala | Arg | Ala | Ala | Cys | Arg | Ala | Ala | Gly | Leu | Gln | Asp | Cys | Thr | Met |
| | | | 100 | | | | | 105 | | | | | 110 | | |

| Leu | Val | Cys | Gly | Asp | Asp | Leu | Val | Val | Ile | Cys | Glu | Ser | Ala | Gly | Val |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gln | Glu | Asp | Ala | Ala | Ser | Leu | Arg | Ala | Phe | Thr | Glu | Ala | Met | Thr | Arg |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Tyr | Ser | Ala | Pro | Pro | Gly | Asp | Pro | Pro | Gln | Pro | Glu | Tyr | Asp | Leu | Glu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Ile | Thr | Ser | Cys | Ser | Ser | Asn | Val | Ser | Val | Ala | His | Asp | Gly | Ala |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | Lys | Arg | Val | Tyr | Tyr | Leu | Thr | Arg | Glu | Phe |
|-----|-----|-----|-----|-----|-----|-----|-----|-----|-----|-----|
|     |     |     | 180 |     |     |     |     | 185 |     |     |

( 2 ) INFORMATION FOR SEQ ID NO:3:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: N ( i v ) ANTI-SENSE: N ( v i ) ORIGINAL SOURCE:
        ( A ) ORGANISM: Hepatitis HCV Virus
        ( B ) STRAIN: CDC &nbs

```
Thr  Thr  Ile  Met  Ala  Lys  Asn  Glu  Val  Phe  Cys  Val  Gln  Pro  Glu  Lys
          20                       25                      30

Gly  Gly  Arg  Lys  Pro  Ala  Arg  Leu  Ile  Val  Phe  Pro  Asp  Leu  Gly  Val
               35                      40                      45

Arg  Val  Cys  Glu  Lys  Met  Ala  Leu  Tyr  Asp  Val  Val  Thr  Lys  Leu  Pro
     50                       55                      60

Leu  Ala  Val  Met  Gly  Ser  Ser  Tyr  Gly  Phe  Gln  Tyr  Ser  Pro  Gly  Gln
65                       70                      75                       80

Arg  Val  Glu  Phe
```

( 2 ) INFORMATION FOR SEQ ID NO:5:

( i ) SEQUENCE CHARACTERISTICS:
        ( A ) LENGTH: 1512 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: N ( i v ) ANTI-SENSE: N ( v i ) ORIGINAL SOURCE:
        ( A ) ORGANISM: Hepatitis C Virus ( v i i ) IMMEDIATE SOURCE:
        ( B ) CLONE: 303-1-4

( i x ) FEATURE:
        ( A ) NAME/KEY: CDS
        ( B ) LOCATION: 1..1512
        ( D ) OTHER INFORMATION:

( x i ) SEQUENCE DESCRIPTION: SEQ ID NO:5:

```
GAA  TTC  TTC  ACA  GAA  TTG  GAC  GGG  GTG  CGC  CTA  CAT  AGG  TTT  GCG  CCC        48
Glu  Phe  Phe  Thr  Glu  Leu  Asp  Gly  Val  Arg  Leu  His  Arg  Phe  Ala  Pro
1              5                        10                       15

CCC  TGC  AAG  CCC  TTG  CTG  CGG  GAG  GAG  GTA  TCA  TTC  AGA  GTA  GGA  CTC        96
Pro  Cys  Lys  Pro  Leu  Leu  Arg  Glu  Glu  Val  Ser  Phe  Arg  Val  Gly  Leu
               20                       25                      30

CAC  GAA  TAC  CCG  GTA  GGG  TCG  CAA  TTA  CCT  TGC  GAG  CCC  GAA  CCG  GAT       144
His  Glu  Tyr  Pro  Val  Gly  Ser  Gln  Leu  Pro  Cys  Glu  Pro  Glu  Pro  Asp
                    35                       40                      45

GTG  GCC  GTG  TTG  ACG  TCC  ATG  CTC  ACT  GAT  CCC  TCC  CAT  ATA  ACA  GCA       192
Val  Ala  Val  Leu  Thr  Ser  Met  Leu  Thr  Asp  Pro  Ser  His  Ile  Thr  Ala
          50                        55                      60

GAG  GCG  GCC  GGG  CGA  AGG  TTG  GCG  AGG  GGA  TCA  CCC  CCC  TCT  GTG  GCC       240
Glu  Ala  Ala  Gly  Arg  Arg  Leu  Ala  Arg  Gly  Ser  Pro  Pro  Ser  Val  Ala
65                       70                      75                       80

AGC  TCC  TCG  GCT  AGC  CAG  CTA  TCC  GCT  CCA  TCT  CTC  AAG  GCA  ACT  TGC       288
Ser  Ser  Ser  Ala  Ser  Gln  Leu  Ser  Ala  Pro  Ser  Leu  Lys  Ala  Thr  Cys
                         85                      90                       95

ACC  GCT  AAC  CAT  GAC  TCC  CCT  GAT  GCT  GAG  CTC  ATA  GAG  GCC  AAC  CTC       336
Thr  Ala  Asn  His  Asp  Ser  Pro  Asp  Ala  Glu  Leu  Ile  Glu  Ala  Asn  Leu
                    100                     105                     110

CTA  TGG  AGG  CAG  GAG  ATG  GGC  GGC  AAC  ATC  ACC  AGG  GTT  GAG  TCA  GAA       384
Leu  Trp  Arg  Gln  Glu  Met  Gly  Gly  Asn  Ile  Thr  Arg  Val  Glu  Ser  Glu
               115                     120                     125

AAC  AAA  GTG  GTG  ATT  CTG  GAC  TCC  TTC  GAT  CCG  CTT  GTG  GCG  GAG  GAG       432
Asn  Lys  Val  Val  Ile  Leu  Asp  Ser  Phe  Asp  Pro  Leu  Val  Ala  Glu  Glu
          130                     135                     140

GAC  GAG  CGG  GAG  ATC  TCC  GTA  CCC  GCA  GAA  ATC  CTG  CGG  AAG  TCT  CGG       480
Asp  Glu  Arg  Glu  Ile  Ser  Val  Pro  Ala  Glu  Ile  Leu  Arg  Lys  Ser  Arg
145                     150                     155                     160
```

| | | | | | | | | | | | | | | | | |
|---|---|---|---|---|---|---|---|---|---|---|---|---|---|---|---|---|
| AGA | TTC | GCC | CAG | GCC | CTG | CCC | GTT | TGG | GCG | CGG | CCG | GAC | TAT | AAC | CCC | 528 |
| Arg | Phe | Ala | Gln 165 | Ala | Leu | Pro | Val | Trp 170 | Ala | Arg | Pro | Asp | Tyr 175 | Asn | Pro | |
| CCG | CTA | GTG | GAG | ACG | TGG | AAA | AAG | CCC | GAC | TAC | GAA | CCA | CCT | GTG | GTC | 576 |
| Pro | Leu | Val | Glu 180 | Thr | Trp | Lys | Lys | Pro 185 | Asp | Tyr | Glu | Pro | Pro 190 | Val | Val | |
| CAT | GGC | TGT | CCG | CTT | CCA | CCT | CCA | AAG | TCC | CCT | CCT | GTG | CCT | CCG | CCT | 624 |
| His | Gly | Cys 195 | Pro | Leu | Pro | Pro | Lys 200 | Ser | Pro | Pro | Val | Pro 205 | Pro | Pro | | |
| CGG | AAG | AAG | CGG | ACG | GTG | GTC | CTC | ACT | GAA | TCA | ACC | CTA | TCT | ACT | GCC | 672 |
| Arg | Lys | Lys 210 | Arg | Thr | Val | Val 215 | Leu | Thr | Glu | Ser | Thr 220 | Leu | Ser | Thr | Ala | |
| TTG | GCC | GAG | CTC | GCC | ACC | AGA | AGC | TTT | GGC | AGC | TCC | TCA | ACT | TCC | GGC | 720 |
| Leu 225 | Ala | Glu | Leu | Ala | Thr 230 | Arg | Ser | Phe | Gly | Ser 235 | Ser | Ser | Thr | Ser | Gly 240 | |
| ATT | ACG | GGC | GAC | AAT | ACG | ACA | ACA | TCC | TCT | GAG | CCC | GCC | CCT | TCT | GGC | 768 |
| Ile | Thr | Gly | Asp | Asn 245 | Thr | Thr | Thr | Ser | Ser 250 | Glu | Pro | Ala | Pro | Ser 255 | Gly | |
| TGC | CCC | CCC | GAC | TCC | GAC | GCT | GAG | TCC | TAT | TCC | TCC | ATG | CCC | CCC | CTG | 816 |
| Cys | Pro | Pro | Asp 260 | Ser | Asp | Ala | Glu | Ser 265 | Tyr | Ser | Ser | Met | Pro 270 | Pro | Leu | |
| GAG | GGG | GAG | CCT | GGG | GAT | CCG | GAT | CTT | AGC | GAC | GGG | TCA | TGG | TCA | ACG | 864 |
| Glu | Gly | Glu 275 | Pro | Gly | Asp | Pro | Asp 280 | Leu | Ser | Asp | Gly | Ser 285 | Trp | Ser | Thr | |
| GTC | AGT | AGT | GAG | GCC | AAC | GCG | GAG | GAT | GTC | GTG | TGC | TGC | TCA | ATG | TCT | 912 |
| Val | Ser 290 | Ser | Glu | Ala | Asn 295 | Ala | Glu | Asp | Val | Val 300 | Cys | Cys | Ser | Met | Ser | |
| TAC | TCT | TGG | ACA | GGC | GCA | CTC | GTC | ACC | CCG | TGC | GCC | GCG | GAA | GAA | CAG | 960 |
| Tyr 305 | Ser | Trp | Thr | Gly | Ala 310 | Leu | Val | Thr | Pro | Cys 315 | Ala | Ala | Glu | Glu | Gln 320 | |
| AAA | CTG | CCC | ATC | AAT | GCA | CTA | AGC | AAC | TCG | TTG | CTA | CGT | CAC | CAC | AAT | 1008 |
| Lys | Leu | Pro | Ile | Asn 325 | Ala | Leu | Ser | Asn | Ser 330 | Leu | Leu | Arg | His | His 335 | Asn | |
| TTG | GTG | TAT | TCC | ACC | ACC | TCA | CGC | AGT | GCT | TGC | CAA | AGG | CAG | AAG | AAA | 1056 |
| Leu | Val | Tyr | Ser 340 | Thr | Thr | Ser | Arg | Ser 345 | Ala | Cys | Gln | Arg | Gln 350 | Lys | Lys | |
| GTC | ACA | TTT | GAC | AGA | CTG | CAA | GTT | CTG | GAC | AGC | CAT | TAC | CAG | GAC | GTA | 1104 |
| Val | Thr | Phe 355 | Asp | Arg | Leu | Gln | Val 360 | Leu | Asp | Ser | His | Tyr 365 | Gln | Asp | Val | |
| CTC | AAG | GAG | GTT | AAA | GCA | GCG | GCG | TCA | AAA | GTG | AAG | GCT | AAC | TTG | CTA | 1152 |
| Leu | Lys | Glu 370 | Val | Lys | Ala | Ala | Ala 375 | Ser | Lys | Val | Lys | Ala 380 | Asn | Leu | Leu | |
| TCC | GTA | GAG | GAA | GCT | TGC | AGC | CTG | ACG | CCC | CCA | CAC | TCA | GCC | AAA | TCC | 1200 |
| Ser 385 | Val | Glu | Glu | Ala | Cys 390 | Ser | Leu | Thr | Pro | Pro 395 | His | Ser | Ala | Lys | Ser 400 | |
| AAG | TTT | GGT | TAT | GGG | GCA | AAA | GAC | GTC | CGT | TGC | CAT | GCC | AGA | AAG | GCC | 1248 |
| Lys | Phe | Gly | Tyr | Gly 405 | Ala | Lys | Asp | Val | Arg 410 | Cys | His | Ala | Arg | Lys 415 | Ala | |
| GTA | ACC | CAC | ATC | AAC | TCC | GTG | TGG | AAA | GAC | CTT | CTG | GAA | GAC | AAT | GTA | 1296 |
| Val | Thr | His | Ile 420 | Asn | Ser | Val | Trp | Lys 425 | Asp | Leu | Leu | Glu | Asp 430 | Asn | Val | |
| ACA | CCA | ATA | GAC | ACT | ACC | ATC | ATG | GCT | AAG | AAC | GAG | GTT | TTC | TGC | GTT | 1344 |
| Thr | Pro | Ile 435 | Asp | Thr | Thr | Ile | Met 440 | Ala | Lys | Asn | Glu | Val 445 | Phe | Cys | Val | |
| CAG | CCT | GAG | AAG | GGG | GGT | CGT | AAG | CCA | GCT | CGT | CTC | ATC | GTG | TTC | CCC | 1392 |
| Gln | Pro | Glu 450 | Lys | Gly | Gly | Arg | Lys 455 | Pro | Ala | Arg | Leu | Ile 460 | Val | Phe | Pro | |
| GAT | CTG | GGC | GTG | CGC | GTG | TGC | GAA | AAG | ATG | GCT | TTG | TAC | GAC | GTG | GTT | 1440 |
| Asp 465 | Leu | Gly | Val | Arg | Val 470 | Cys | Glu | Lys | Met | Ala 475 | Leu | Tyr | Asp | Val | Val 480 | |
| ACC | AAG | CTC | CCC | TTG | GCC | GTG | ATG | GGA | AGC | TCC | TAC | GGA | TTC | CAA | TAC | 1488 |

|     |     |     |     |     |     |     |     |     |     |     |     |     |     |     |      |
|-----|-----|-----|-----|-----|-----|-----|-----|-----|-----|-----|-----|-----|-----|-----|------|
| Thr | Lys | Leu | Pro | Leu | Ala | Val | Met | Gly | Ser | Ser | Tyr | Gly | Phe | Gln | Tyr  |
|     |     |     |     | 485 |     |     |     | 490 |     |     |     |     |     | 495 |      |

```
TCA CCA GGA CAG CGG GTT GAA TTC                                          1512
Ser Pro Gly Gln Arg Val Glu Phe
            500
```

( 2 ) INFORMATION FOR SEQ ID NO:6:

( i ) SEQUENCE CHARACTERISTICS:
        ( A ) LENGTH: 504 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Glu | Phe | Phe | Thr | Glu | Leu | Asp | Gly | Val | Arg | Leu | His | Arg | Phe | Ala | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Cys | Lys | Pro | Leu | Leu | Arg | Glu | Glu | Val | Ser | Phe | Arg | Val | Gly | Leu |
|     |     |     | 20  |     |     |     |     | 25  |     |     |     |     | 30  |     |     |
| His | Glu | Tyr | Pro | Val | Gly | Ser | Gln | Leu | Pro | Cys | Glu | Pro | Glu | Pro | Asp |
|     |     | 35  |     |     |     |     | 40  |     |     |     |     | 45  |     |     |     |
| Val | Ala | Val | Leu | Thr | Ser | Met | Leu | Thr | Asp | Pro | Ser | His | Ile | Thr | Ala |
|     | 50  |     |     |     |     | 55  |     |     |     |     | 60  |     |     |     |     |
| Glu | Ala | Ala | Gly | Arg | Arg | Leu | Ala | Arg | Gly | Ser | Pro | Pro | Ser | Val | Ala |
| 65  |     |     |     |     | 70  |     |     |     |     | 75  |     |     |     |     | 80  |
| Ser | Ser | Ser | Ala | Ser | Gln | Leu | Ser | Ala | Pro | Ser | Leu | Lys | Ala | Thr | Cys |
|     |     |     |     | 85  |     |     |     |     | 90  |     |     |     |     | 95  |     |
| Thr | Ala | Asn | His | Asp | Ser | Pro | Asp | Ala | Glu | Leu | Ile | Glu | Ala | Asn | Leu |
|     |     |     | 100 |     |     |     |     | 105 |     |     |     |     | 110 |     |     |
| Leu | Trp | Arg | Gln | Glu | Met | Gly | Gly | Asn | Ile | Thr | Arg | Val | Glu | Ser | Glu |
|     |     | 115 |     |     |     |     | 120 |     |     |     |     | 125 |     |     |     |
| Asn | Lys | Val | Val | Ile | Leu | Asp | Ser | Phe | Asp | Pro | Leu | Val | Ala | Glu | Glu |
|     | 130 |     |     |     |     | 135 |     |     |     |     | 140 |     |     |     |     |
| Asp | Glu | Arg | Glu | Ile | Ser | Val | Pro | Ala | Glu | Ile | Leu | Arg | Lys | Ser | Arg |
| 145 |     |     |     |     | 150 |     |     |     |     | 155 |     |     |     |     | 160 |
| Arg | Phe | Ala | Gln | Ala | Leu | Pro | Val | Trp | Ala | Arg | Pro | Asp | Tyr | Asn | Pro |
|     |     |     |     | 165 |     |     |     |     | 170 |     |     |     |     | 175 |     |
| Pro | Leu | Val | Glu | Thr | Trp | Lys | Lys | Pro | Asp | Tyr | Glu | Pro | Pro | Val | Val |
|     |     |     | 180 |     |     |     |     | 185 |     |     |     |     | 190 |     |     |
| His | Gly | Cys | Pro | Leu | Pro | Pro | Pro | Lys | Ser | Pro | Pro | Val | Pro | Pro | Pro |
|     |     | 195 |     |     |     |     | 200 |     |     |     |     | 205 |     |     |     |
| Arg | Lys | Lys | Arg | Thr | Val | Val | Leu | Thr | Glu | Ser | Thr | Leu | Ser | Thr | Ala |
|     | 210 |     |     |     |     | 215 |     |     |     |     | 220 |     |     |     |     |
| Leu | Ala | Glu | Leu | Ala | Thr | Arg | Ser | Phe | Gly | Ser | Ser | Ser | Thr | Ser | Gly |
| 225 |     |     |     |     | 230 |     |     |     |     | 235 |     |     |     |     | 240 |
| Ile | Thr | Gly | Asp | Asn | Thr | Thr | Thr | Ser | Ser | Glu | Pro | Ala | Pro | Ser | Gly |
|     |     |     |     | 245 |     |     |     |     | 250 |     |     |     |     | 255 |     |
| Cys | Pro | Pro | Asp | Ser | Asp | Ala | Glu | Ser | Tyr | Ser | Ser | Met | Pro | Pro | Leu |
|     |     |     | 260 |     |     |     |     | 265 |     |     |     |     | 270 |     |     |
| Glu | Gly | Glu | Pro | Gly | Asp | Pro | Asp | Leu | Ser | Asp | Gly | Ser | Trp | Ser | Thr |
|     |     | 275 |     |     |     |     | 280 |     |     |     |     | 285 |     |     |     |
| Val | Ser | Ser | Glu | Ala | Asn | Ala | Glu | Asp | Val | Val | Cys | Cys | Ser | Met | Ser |
|     | 290 |     |     |     |     | 295 |     |     |     |     | 300 |     |     |     |     |
| Tyr | Ser | Trp | Thr | Gly | Ala | Leu | Val | Thr | Pro | Cys | Ala | Ala | Glu | Glu | Gln |
| 305 |     |     |     |     | 310 |     |     |     |     | 315 |     |     |     |     | 320 |
| Lys | Leu | Pro | Ile | Asn | Ala | Leu | Ser | Asn | Ser | Leu | Leu | Arg | His | His | Asn |
|     |     |     |     | 325 |     |     |     |     | 330 |     |     |     |     | 335 |     |

| | | | | | | | | | | | | | | |
|---|---|---|---|---|---|---|---|---|---|---|---|---|---|---|
|Leu|Val|Tyr|Ser<br>340|Thr|Thr|Ser|Arg|Ser<br>345|Ala|Cys|Gln|Arg|Gln<br>350|Lys|Lys|
|Val|Thr|Phe<br>355|Asp|Arg|Leu|Gln|Val<br>360|Leu|Asp|Ser|His|Tyr<br>365|Gln|Asp|Val|
|Leu|Lys<br>370|Glu|Val|Lys|Ala|Ala<br>375|Ala|Ser|Lys|Val|Lys<br>380|Ala|Asn|Leu|Leu|
|Ser<br>385|Val|Glu|Glu|Ala|Cys<br>390|Ser|Leu|Thr|Pro|Pro<br>395|His|Ser|Ala|Lys|Ser<br>400|
|Lys|Phe|Gly|Tyr|Gly<br>405|Ala|Lys|Asp|Val|Arg<br>410|Cys|His|Ala|Arg|Lys<br>415|Ala|
|Val|Thr|His|Ile<br>420|Asn|Ser|Val|Trp|Lys<br>425|Asp|Leu|Leu|Glu|Asp<br>430|Asn|Val|
|Thr|Pro|Ile<br>435|Asp|Thr|Thr|Ile|Met<br>440|Ala|Lys|Asn|Glu|Val<br>445|Phe|Cys|Val|
|Gln|Pro<br>450|Glu|Lys|Gly|Gly|Arg<br>455|Lys|Pro|Ala|Arg|Leu<br>460|Ile|Val|Phe|Pro|
|Asp<br>465|Leu|Gly|Val|Arg|Val<br>470|Cys|Glu|Lys|Met|Ala<br>475|Leu|Tyr|Asp|Val|Val<br>480|
|Thr|Lys|Leu|Pro|Leu<br>485|Ala|Val|Met|Gly|Ser<br>490|Ser|Tyr|Gly|Phe|Gln<br>495|Tyr|
|Ser|Pro|Gly|Gln<br>500|Arg|Val|Glu|Phe| | | | | | | | |

( 2 ) INFORMATION FOR SEQ ID NO:7:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: N ( i v ) ANTI-SENSE: N ( v i ) ORIGINAL SOURCE:
        ( A ) ORGANISM: Hepatitis C Virus
        ( B ) STRAIN: CDC
        ( C ) INDIVIDUAL ISOLATE: Rodney ( v i i ) IMMEDIATE SOURCE:
        ( B ) CLONE: 409-1-1 (c-a)

( i x ) FEATURE:
        ( A ) NAME/KEY: CDS
        ( B ) LOCATION: 1..477
        ( D ) OTHER INFORMATION:

( x i ) SEQUENCE DESCRIPTION: SEQ ID NO:7:

| | | | | | | | | | | | | | | | | |
|---|---|---|---|---|---|---|---|---|---|---|---|---|---|---|---|---|
|GAA|TTC|CGC|ACG|CCC|GCC|GAG|ACT|ACA|GTT|AGG|CTA|CGG|GCG|TAC|ATG|48|
|Glu|Phe|Arg|Thr|Pro<br>5|Ala|Glu|Thr|Thr|Val<br>10|Arg|Leu|Arg|Ala|Tyr<br>15|Met| |
|1| | | | | | | | | | | | | | | | |
|AAC|ACT|CCG|GGG|CTT|CCC|GTG|TGC|CAG|GAC|GGA|ATT|CCG|TCC|CCG|TCC|96|
|Asn|Thr|Pro|Gly<br>20|Leu|Pro|Val|Cys|Gln<br>25|Asp|Gly|Ile|Pro|Ser<br>30|Pro|Ser| |
|ACC|ACC|GGA|GAG|ATC|CCT|TTT|TAC|GGC|AAG|GCT|ATC|CCC|CTC|GAA|GTA|144|
|Thr|Thr|Gly<br>35|Glu|Ile|Pro|Phe|Tyr<br>40|Gly|Lys|Ala|Ile|Pro<br>45|Leu|Glu|Val| |
|ATC|AAG|GGG|GGG|AGA|CAT|CTC|ATC|TTC|TGT|CAT|TCA|AAG|AAG|AAG|TGC|192|
|Ile|Lys<br>50|Gly|Gly|Arg|His|Leu<br>55|Ile|Phe|Cys|His|Ser<br>60|Lys|Lys|Lys|Cys| |
|GAC|GAA|CTC|GCC|GCA|AAG|CTG|GTC|GCA|TTG|GGC|ATC|AAT|GCC|GTG|GCC|240|
|Asp|Glu|Leu|Ala|Ala<br>70|Lys|Leu|Val|Ala|Leu<br>75|Gly|Ile|Asn|Ala|Val<br>80|Ala| |
|65| | | | | | | | | | | | | | | | |

```
TAC TAC CGC GGT CTT GAC GTG TCC GTC ATC CCG ACC AGC GGC GAT GTT         288
Tyr Tyr Arg Gly Leu Asp Val Ser Val Ile Pro Thr Ser Gly Asp Val
            85              90                      95

GTC GTC GTG GCA ACC GAT GCC CTC ATG ACC GGC TAT ACC GGC GAC TTC         336
Val Val Val Ala Thr Asp Ala Leu Met Thr Gly Tyr Thr Gly Asp Phe
            100             105                     110

GAC TCG GTG ATA GAC TGC AAT ACG TGT GTC ACC CAG ACA GTC GAT TTC         384
Asp Ser Val Ile Asp Cys Asn Thr Cys Val Thr Gln Thr Val Asp Phe
            115             120                     125

AGC CTT GAC CCT ACC TTC ACC ATT GAG ACA ATC ACG CTC CCC CAG GAT         432
Ser Leu Asp Pro Thr Phe Thr Ile Glu Thr Ile Thr Leu Pro Gln Asp
            130             135                     140

GCT GTC TCC CGC ACT CAA CGT CGG GGC AGG ACT GGC ACG GAA TTC             477
Ala Val Ser Arg Thr Gln Arg Arg Gly Arg Thr Gly Thr Glu Phe
145             150                     155
```

( 2 ) INFORMATION FOR SEQ ID NO:8:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Glu Phe Arg Thr Pro Ala Glu Thr Thr Val Arg Leu Arg Ala Tyr Met
1               5                   10                      15

Asn Thr Pro Gly Leu Pro Val Cys Gln Asp Gly Ile Pro Ser Pro Ser
                20                  25                  30

Thr Thr Gly Glu Ile Pro Phe Tyr Gly Lys Ala Ile Pro Leu Glu Val
            35              40                      45

Ile Lys Gly Gly Arg His Leu Ile Phe Cys His Ser Lys Lys Lys Cys
    50                  55                  60

Asp Glu Leu Ala Ala Lys Leu Val Ala Leu Gly Ile Asn Ala Val Ala
65                  70                  75                      80

Tyr Tyr Arg Gly Leu Asp Val Ser Val Ile Pro Thr Ser Gly Asp Val
            85                  90                      95

Val Val Val Ala Thr Asp Ala Leu Met Thr Gly Tyr Thr Gly Asp Phe
            100                 105                     110

Asp Ser Val Ile Asp Cys Asn Thr Cys Val Thr Gln Thr Val Asp Phe
            115                 120                     125

Ser Leu Asp Pro Thr Phe Thr Ile Glu Thr Ile Thr Leu Pro Gln Asp
            130                 135                     140

Ala Val Ser Arg Thr Gln Arg Arg Gly Arg Thr Gly Thr Glu Phe
145             150                     155
```

( 2 ) INFORMATION FOR SEQ ID NO:9:

( i ) SEQUENCE CHARACTERISTICS:
        ( A ) LENGTH: 558 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: N ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: 409-1-1 (abc)

(ix) FEATURE:
  (A) NAME/KEY: CDS
  (B) LOCATION: 1..558
  (D) OTHER INFORMATION:

(xi) SEQUENCE DESCRIPTION: SEQ ID NO:9:

| | | | | | | | | | | | | | | | | |
|---|---|---|---|---|---|---|---|---|---|---|---|---|---|---|---|---|
| TCC | ACC | ACC | GGA | GAG | ATC | CCT | TTT | TAC | GGC | AAG | GCT | ATC | CCC | CTC | GAA | 48 |
| Ser | Thr | Thr | Gly | Glu | Ile | Pro | Phe | Tyr | Gly | Lys | Ala | Ile | Pro | Leu | Glu | |
| 1 | | | | 5 | | | | | 10 | | | | | 15 | | |
| GTA | ATC | AAG | GGG | GGG | AGA | CAT | CTC | ATC | TTC | TGT | CAT | TCA | AAG | AAG | AAG | 96 |
| Val | Ile | Lys | Gly | Gly | Arg | His | Leu | Ile | Phe | Cys | His | Ser | Lys | Lys | Lys | |
| | | | 20 | | | | | 25 | | | | | 30 | | | |
| TGC | GAC | GAA | CTC | GCC | GCA | AAG | CTG | GTC | GCA | TTG | GGC | ATC | AAT | GCC | GTG | 144 |
| Cys | Asp | Glu | Leu | Ala | Ala | Lys | Leu | Val | Ala | Leu | Gly | Ile | Asn | Ala | Val | |
| | | 35 | | | | | 40 | | | | | 45 | | | | |
| GCC | TAC | TAC | CGC | GGT | CTT | GAC | GTG | TCC | GTC | ATC | CCG | ACC | AGC | GGC | GAT | 192 |
| Ala | Tyr | Tyr | Arg | Gly | Leu | Asp | Val | Ser | Val | Ile | Pro | Thr | Ser | Gly | Asp | |
| | 50 | | | | | 55 | | | | | 60 | | | | | |
| GTT | GTC | GTC | GTG | GCA | ACC | GAT | GCC | CTC | ATG | ACC | GGC | TAT | ACC | GGC | GAC | 240 |
| Val | Val | Val | Val | Ala | Thr | Asp | Ala | Leu | Met | Thr | Gly | Tyr | Thr | Gly | Asp | |
| 65 | | | | | 70 | | | | | 75 | | | | | 80 | |
| TTC | GAC | TCG | GTG | ATA | GAC | TGC | AAT | ACG | TGT | GTC | ACC | CAG | ACA | GTC | GAT | 288 |
| Phe | Asp | Ser | Val | Ile | Asp | Cys | Asn | Thr | Cys | Val | Thr | Gln | Thr | Val | Asp | |
| | | | | 85 | | | | | 90 | | | | | 95 | | |
| TTC | AGC | CTT | GAC | CCT | ACC | TTC | ACC | ATT | GAG | ACA | ATC | ACG | CTC | CCC | CAG | 336 |
| Phe | Ser | Leu | Asp | Pro | Thr | Phe | Thr | Ile | Glu | Thr | Ile | Thr | Leu | Pro | Gln | |
| | | | 100 | | | | | 105 | | | | | 110 | | | |
| GAT | GCT | GTC | TCC | CGC | ACT | CAA | CGT | CGG | GGC | AGG | ACT | GGC | AGG | GGG | AAG | 384 |
| Asp | Ala | Val | Ser | Arg | Thr | Gln | Arg | Arg | Gly | Arg | Thr | Gly | Arg | Gly | Lys | |
| | | 115 | | | | | 120 | | | | | 125 | | | | |
| CCA | GGC | ATC | TAC | AGA | TTT | GTG | GCA | CCG | GGG | GAG | CGC | CCC | TCC | GGC | ATG | 432 |
| Pro | Gly | Ile | Tyr | Arg | Phe | Val | Ala | Pro | Gly | Glu | Arg | Pro | Ser | Gly | Met | |
| | 130 | | | | | 135 | | | | | 140 | | | | | |
| TTC | GAC | TCG | TCC | GTC | CTC | TGT | GAG | TGC | TAT | GAC | GCA | GGC | TGT | GCT | TGG | 480 |
| Phe | Asp | Ser | Ser | Val | Leu | Cys | Glu | Cys | Tyr | Asp | Ala | Gly | Cys | Ala | Trp | |
| 145 | | | | | 150 | | | | | 155 | | | | | 160 | |
| TAT | GAG | CTC | ACG | CCC | GCC | GAG | ACT | ACA | GTT | AGG | CTA | CGA | GCG | TAC | ATG | 528 |
| Tyr | Glu | Leu | Thr | Pro | Ala | Glu | Thr | Thr | Val | Arg | Leu | Arg | Ala | Tyr | Met | |
| | | | | 165 | | | | | 170 | | | | | 175 | | |
| AAC | ACC | CCG | GGG | CTT | CCC | GTG | TGC | CAG | GAC | | | | | | | 558 |
| Asn | Thr | Pro | Gly | Leu | Pro | Val | Cys | Gln | Asp | | | | | | | |
| | | | 180 | | | | | 185 | | | | | | | | |

(2) INFORMATION FOR SEQ ID NO:10:

(i) SEQUENCE CHARACTERISTICS:
    (A) LENGTH: 186 amino acids
    (B) TYPE: amino acid
    (D) TOPOLOGY: linear (ii) MOLECULE TYPE: protein (xi) SEQUENCE DESCRIPTION: SEQ ID NO:10:

| | | | | | | | | | | | | | | | |
|---|---|---|---|---|---|---|---|---|---|---|---|---|---|---|---|
| Ser | Thr | Thr | Gly | Glu | Ile | Pro | Phe | Tyr | Gly | Lys | Ala | Ile | Pro | Leu | Glu |
| 1 | | | | 5 | | | | | 10 | | | | | 15 | |
| Val | Ile | Lys | Gly | Gly | Arg | His | Leu | Ile | Phe | Cys | His | Ser | Lys | Lys | Lys |
| | | | 20 | | | | | 25 | | | | | 30 | | |
| Cys | Asp | Glu | Leu | Ala | Ala | Lys | Leu | Val | Ala | Leu | Gly | Ile | Asn | Ala | Val |
| | | 35 | | | | | 40 | | | | | 45 | | | |
| Ala | Tyr | Tyr | Arg | Gly | Leu | Asp | Val | Ser | Val | Ile | Pro | Thr | Ser | Gly | Asp |
| | 50 | | | | | 55 | | | | | 60 | | | | |
| Val | Val | Val | Val | Ala | Thr | Asp | Ala | Leu | Met | Thr | Gly | Tyr | Thr | Gly | Asp |
| 65 | | | | | 70 | | | | | 75 | | | | | 80 |

```
Phe Asp Ser Val Ile Asp Cys Asn Thr Cys Val Thr Gln Thr Val Asp
                85              90              95
Phe Ser Leu Asp Pro Thr Phe Thr Ile Glu Thr Ile Thr Leu Pro Gln
            100             105             110
Asp Ala Val Ser Arg Thr Gln Arg Arg Gly Arg Thr Gly Arg Gly Lys
            115             120             125
Pro Gly Ile Tyr Arg Phe Val Ala Pro Gly Glu Arg Pro Ser Gly Met
        130             135             140
Phe Asp Ser Ser Val Leu Cys Glu Cys Tyr Asp Ala Gly Cys Ala Trp
145             150             155             160
Tyr Glu Leu Thr Pro Ala Glu Thr Thr Val Arg Leu Arg Ala Tyr Met
            165             170             175
Asn Thr Pro Gly Leu Pro Val Cys Gln Asp
            180             185
```